(12) United States Patent
Khurana

(10) Patent No.: US 7,998,513 B1
(45) Date of Patent: Aug. 16, 2011

(54) ASCORBATE MONITORING AND CONTROL SYSTEM

(75) Inventor: Karan Khurana, Calabasas, CA (US)

(73) Assignee: Primordial Diagnostics, Inc., Van Nuys, CA (US)

( * ) Notice: Subject to any disclaimer, the term of this patent is extended or adjusted under 35 U.S.C. 154(b) by 524 days.

(21) Appl. No.: 12/167,889

(22) Filed: Jul. 3, 2008

Related U.S. Application Data

(60) Provisional application No. 60/948,900, filed on Jul. 10, 2007.

(51) Int. Cl.
*A23L 1/27* (2006.01)
*A23B 4/26* (2006.01)

(52) U.S. Cl. ......... 426/231; 426/267; 426/321; 426/541

(58) Field of Classification Search .................. 426/231, 426/267–268, 321, 541; 436/161, 43, 50–52; 73/1.02, 1.03, 79; 700/267, 1; 422/50, 68.1, 422/82.03, 75; 702/1, 22–23
See application file for complete search history.

(56) References Cited

U.S. PATENT DOCUMENTS

| | | | | |
|---|---|---|---|---|
| 3,754,938 A | * | 8/1973 | Ponting | 426/321 |
| 3,920,397 A | * | 11/1975 | Small et al. | 436/79 |
| 4,109,314 A | * | 8/1978 | Meyer et al. | 702/23 |
| 4,199,323 A | * | 4/1980 | Miller et al. | 436/150 |
| 4,476,112 A | * | 10/1984 | Aversano | 426/268 |
| 4,724,216 A | | 2/1988 | Young et al. | |
| 4,883,679 A | | 11/1989 | Sewon | |
| 4,988,522 A | | 1/1991 | Warren | |
| 5,332,589 A | * | 7/1994 | Hinnergardt et al. | 426/231 |
| 5,702,579 A | | 12/1997 | Veits | |
| 5,863,584 A | | 1/1999 | Thomas, Jr. et al. | |
| 5,939,117 A | | 8/1999 | Chen et al. | |
| 6,749,875 B2 | | 6/2004 | Selleck | |
| 6,896,921 B2 | * | 5/2005 | Groves et al. | 426/231 |
| 7,186,376 B2 | | 3/2007 | Iverson et al. | |
| 7,349,760 B2 | * | 3/2008 | Wei et al. | 700/267 |
| 7,601,266 B2 | | 10/2009 | Iverson | |
| 7,851,002 B2 | * | 12/2010 | Hekal et al. | 426/310 |
| 2001/0048958 A1 | * | 12/2001 | Funk | 426/231 |
| 2007/0042093 A1 | * | 2/2007 | Lidster et al. | 426/321 |
| 2008/0175963 A1 | * | 7/2008 | Pope | 426/231 |

FOREIGN PATENT DOCUMENTS

| | | |
|---|---|---|
| EP | 0 304 151 B1 | 12/1993 |
| WO | WO 94/12041 | 6/1994 |

OTHER PUBLICATIONS

"Quantitative Analysis of Calcium Ascorbate Content in Vitamin C Using Analytical Spectral Devices' Labspec Pro NIR Analyzer", Internet Retrieved on Jun. 19, 2007, [URL:www.asdi.com/Vitamin%20C%20article.pdf].

\* cited by examiner

*Primary Examiner* — Drew E Becker
*Assistant Examiner* — Steven Leff
(74) *Attorney, Agent, or Firm* — Michael Blaine Brooks, PC; Michael B. Brooks

(57) ABSTRACT

Method and system embodiments of the present invention control the ascorbate concentration in produce treatments and particularly are exemplified in fresh cut fruit and vegetable treatments via measured refractivity and/or electrical conductivity of, and/or calcium ions present in, the treatment solution.

40 Claims, 10 Drawing Sheets

ASCORBATE MONITORING AND CONTROL SYSTEM

CROSS-REFERENCE TO RELATED APPLICATIONS

This application claims the benefit of U.S. Provisional Patent Application No. 60/948,900 filed Jul. 10, 2007, the contents of which, including all appendices, are hereby incorporated by reference herein for all purposes.

BACKGROUND

1. Field of Endeavor

The invention, in its several embodiments, pertains generally to the measurement and control of ascorbate in liquid solutions and particularly to the monitoring and control of ascorbate based on refractivity, and/or the electrical conductivity, of a liquid solution sample and/or the monitoring and control of calcium ascorbate based on the concentration of calcium ions in the liquid solution.

2. State of Technology

Ascorbate is a salt, e.g., calcium ascorbate and sodium ascorbate, or other derivatives of ascorbic acid. Ascorbate compound solution is used as an anti-oxidant dip for the prevention of the browning of fruit and vegetable surfaces, and preserving the appearance, texture, crispness and color of fresh cut or minimally processed fruits and vegetables, such as apples. Proper management via continuous or continual monitoring and control of ascorbate concentration levels in the dip tank during processing enhances the effectiveness of the ascorbate as a preservative for fresh fruit and vegetables. Brine solutions containing ascorbic acid have been proposed in U.S. Pat. No. 4,883,679 to Sewón. Compositions of edible ingredients in solution and a dipping process for treating freshly cut surfaces of edible plants have been proposed in U.S. Pat. No. 4,988,522 to Warren. Methods of preserving fresh fruit have been proposed such as: (a) using calcium ascorbate according to U.S. Pat. No. 5,939,117 to Chen et al.; (b) using ascorbic acid according to U.S. Pat. No. 6,749,875 to Selleck; and (c) using calcium ions and ascorbate ions according to WO 94/12041 by Lidden.

Calcium ion concentrations in solutions can be measured based on the electrical properties of the solution, particularly by electrodes that are ion specific. Calcium ion-specific electrodes have been proposed for use in the measuring of calcium ions, e.g., as disclosed by U.S. Pat. No. 4,724,216 to Young et al., and by EP0304151 to Musacchio et al.

A refractometer is an instrument that measures the refractive index based on a principle that the refractive index of a solution increases in proportion to the concentration of the solute in the solution. As illustrated in FIG. 1, if the refractive index of air under atmospheric pressure is unity, when light enters medium x, the ratio of the sine of the incident angle, $\alpha$, measured against the phase boundary to the sine of the refracting angle, $\beta$, is called the refractive index of the medium, x. Brix is related to the concentration of dissolved solids, e.g., sucrose, in a fluid and is related to the specific gravity of the liquid. Because the specific gravity of sucrose solutions is well known, it can also be measured by refractometers. Modern Brix meters are typically digital refractometers that calculate the Brix value based on a refractive index. A Brix percentage scale is recommended by the International Committee of Uniform Method of Sugar Analysis (ICUMSA). Brix meters are used in the food industry for measuring the approximate amount of sugars in fruits, vegetables, juices, wine, soft drinks and in the sugar manufacturing industry.

Electrical conductivity is used as a basis for assessing the progress of electrodialysis in the making of ascorbic acid as proposed in U.S. Pat. No. 5,702,579 by Veits. Conductivity is the ability of a material to conduct electric current. Instruments that measure conductivity may employ an anode and a cathode as two plates of a circuit having an electrical potential applied across the plates, which may be via a sine wave voltage, and the current that passes through the solution and completes the circuit is measured. FIG. 2 is a depiction of an aspect of an exemplary instrument for measuring conductivity employing an anode and a cathode as two plates. The graphs shown in FIGS. 3A and 3B illustrate the relationship between conductivity and ion concentration for two common solutions. Notice that the graph is linear for a sodium chloride solution, but nonlinear for highly concentrated sulfuric acid. Ionic interactions can alter the linear relationship between conductivity and concentration in some highly concentrated solutions. FIG. 3A is a graphical depiction of the relationship of the ion concentration of sodium chloride in solution with electrical conductivity. FIG. 3B is a graphical depiction of the relationship of the ion concentration of sulfuric acid in solution with electrical conductivity. FIG. 4 is a graphical depiction of an in-line placement of a circuit element of an electrical conductivity measuring device.

Most conductivity meters have a two-electrode cell, as in FIG. 2, available in either dip or flow-through styles. The electrode surface is usually platinum, titanium, gold-plated nickel, or graphite. Four-electrode cells use a reference voltage to compensate for any polarization or fouling of the electrode plates. The reference voltage ensures that measurements indicate actual conductivity independent of electrode condition, resulting in higher accuracy for measuring over wide ranges. Conductivity (G), is the inverse of resistivity (R), i.e., G=1/R, and conductivity may be determined from the voltage and current values according to Ohm's law (V=IR) where since the charge on the ions in solution facilitates the conductance of electrical currents, the conductivity of a solution may be proportional to the solution's ion concentration.

Conductivity may be measured via sensor elements directly immersed in the solution as in FIG. 2. Alternatively, one or more of the sensor elements may be encased in protective material before immersion or placed outside of the direct flow path. FIG. 4 is a graphical depiction of an in-line placement of a circuit element of an electrical conductivity measuring device. Toroidal coils, having an annular presentation to a flow line, may be positioned or encased so as not to be in contact with the solution. Toroidal coils may be either encased in a polymeric material or are external to a flow through cell. A toroidal conductivity measurement is made by passing an AC current through a toroidal drive coil, which induces a current in the electrolyte solution. This induced solution current, in turn, induces a current in a second toroidal coil, called the pick-up toroid. The amount of current induced in the pick-up toroid is proportional to the solution conductivity.

SUMMARY

Method and system embodiments of the present invention control the ascorbate concentration in produce treatments and particularly are exemplified in fresh cut fruit and vegetable treatments via measured refractivity and/or electrical conductivity of, and/or calcium ions present in, the treatment solution. Method and system embodiments of the present invention control the ascorbate concentration in produce treatments and particularly are exemplified in fresh cut fruit and vegetable treatments via measured refractivity and/or electrical conductivity of the treatment solution and/or the presence of calcium ions measured via a calcium ion-specific electrode. For example, a method embodiment of the present invention includes a process for controlling ascorbate concentration of fresh produce treatment comprising, not necessarily in the following order, the steps of: (1) providing a fresh produce treatment comprised of water and ascorbate; (2) measuring via a refractive index sensor, a first ascorbate concentration in a first sample comprised of the fresh produce treatment; (3) measuring via an electrical conductivity, a second ascorbate concentration in at least one of: the first sample comprised of the fresh produce treatment and a second sample comprised of the fresh produce treatment; (4) determining via a calcium ion-specific electrode, a third ascorbate concentration in at least one of: the first sample comprised of the fresh produce treatment, the second sample comprised of the fresh produce treatment, and a third sample comprised of the fresh produce treatment; (5) generating a measured ascorbate concentration based on the first measured ascorbate concentration, the second measured ascorbate concentration, and the third, i.e. the determined, ascorbate concentration; (6) comparing the generated ascorbate concentration with a control set point value to generate a difference value; and (7) if the difference value is above a threshold, then feeding ascorbate into the fresh produce treatment. In some embodiments of the process, the step of feeding ascorbate into the fresh produce treatment comprises feeding ascorbate in incremental amounts via a pulsed valve. In other embodiments of the process, the step of feeding ascorbate into the fresh produce treatment comprises feeding ascorbate in incremental amounts via a pulsed valve executing pulses proportionally cycled based on the difference value. In still other embodiments of the process, the step of feeding ascorbate into the fresh produce treatment comprises feeding ascorbate in via a pump having pumping cycles proportionally based on the difference value.

An exemplary system for controlling ascorbate concentration in a fresh produce treatment may comprise: (a) the fresh produce treatment comprised of water, and ascorbate ions; (b) a prism sensor to measure refractive index in the fresh produce treatment; (c) a circuit to measure electrical conductivity of the fresh produce treatment; (d) a calcium ion-specific electrode to measure calcium ions of the fresh produce treatment; and (e) a controller having a processor and addressable memory and having a converter function adapted to read a concentration output from the prism sensor, adapted to read an output from an electrical conductivity circuit and adapted to read an output from the calcium ion-specific electrode, and wherein the controller is adapted to transmit ascorbate feed commands to a feed pump in response to the concentration difference. In some system embodiments, the controller may be further adapted to condition the concentration difference via a threshold hysteresis and a delay to generate the one or more ascorbate feed commands. In other system embodiments, the feed pump may be further adapted to output incremental amounts from an ascorbate source via a pulsed valve executing pulses proportionally cycled based on the difference value. In still other system embodiments, the feed pump may be further adapted to output ascorbate from an ascorbate source by executing pumping cycles proportionally based on the difference value.

Method and system embodiments of the present invention control the ascorbate concentration in produce treatments and particularly are exemplified in fresh cut fruit and vegetable treatments via measured refractivity and/or electrical conductivity of the treatment solution. For example, a method embodiment of the present invention includes a process for controlling ascorbate concentration of fresh produce treatment comprising, not necessarily in the following order, the steps of: (1) providing a fresh produce treatment comprised of water and ascorbate; (2) measuring via a refractive index sensor, a first ascorbate concentration in a first sample comprised of the fresh produce treatment; (3) measuring via an electrical conductivity, a second ascorbate concentration in at least one of: the first sample comprised of the fresh produce treatment and a second sample comprised of the fresh produce treatment; (4) generating a measured ascorbate concentration based on the first measured ascorbate concentration and the second measured ascorbate concentration; (5) comparing the measured ascorbate concentration with a control set point value to generate a difference value; and (6) if the difference value is above a threshold, then feeding ascorbate into the fresh produce treatment. In some embodiments of the process, the step of feeding ascorbate into the fresh produce treatment comprises feeding ascorbate in incremental amounts via a pulsed valve. In other embodiments of the process, the step of feeding ascorbate into the fresh produce treatment comprises feeding ascorbate in incremental amounts via a pulsed valve executing pulses proportionally cycled based on the difference value. In still other embodiments of the process, the step of feeding ascorbate into the fresh produce treatment comprises feeding ascorbate in via a pump having pumping cycles proportionally based on the difference value.

An exemplary system for controlling ascorbate concentration in a fresh produce treatment may comprise: (a) the fresh produce treatment comprised of water, and ascorbate ions; (b) a prism sensor to measure refractive index in the fresh produce treatment; (c) a circuit to measure electrical conductivity of the fresh produce treatment; and (d) a controller having a processor and addressable memory and having a converter function adapted to read a concentration output from the prism sensor and adapted to read an output from an electrical conductivity circuit and wherein the controller is adapted to transmit ascorbate feed commands to a feed pump in response to the concentration difference. In some system embodiments, the controller may be further adapted to condition the concentration difference via a threshold hysteresis and a delay to generate the one or more ascorbate feed commands. In other system embodiments, the feed pump may be further adapted to output incremental amounts from an ascorbate source via a pulsed valve executing pulses proportionally cycled based on the difference value. In still other system embodiments, the feed pump may be further adapted to output ascorbate from an ascorbate source by executing pumping cycles proportionally based on the difference value.

Method and system embodiments of the present invention control the ascorbate concentration in produce treatments and particularly are exemplified in fresh cut fruit and vegetable treatments via measured calcium ion concentrations. For example, a process for controlling ascorbate concentration of fresh produce treatment may comprise:
(1) providing a fresh produce treatment comprised of water and ascorbic acid; (2) measuring, via a refractometer, the Brix percentage of a sample comprised of the fresh produce treatment; (3) comparing an ascorbate concentration, derived from the measured Brix percentage, with a control set point value to generate a difference value; and (4) if the difference value is above a threshold, then feeding ascorbate into the fresh produce treatment. In some embodiments of the process, the step of feeding ascorbate into the fresh produce treatment comprises feeding ascorbate in incremental amounts via a pulsed valve. In other embodiments of the process, the step of feeding ascorbate into the fresh produce treatment comprises feeding ascorbate in incremental amounts via a pulsed valve executing pulses proportionally cycled based on the difference value. In still other embodiments of the process, the step of feeding ascorbate into the fresh produce treatment comprises feeding ascorbate in via a pump having pumping cycles proportionally based on the difference value.

An exemplary system for controlling ascorbate concentration in a fresh produce treatment may comprise: (a) the fresh produce treatment comprised of water, calcium ions and ascorbic acid; (b) a refractometer adapted to sense Brix percentages in the fresh produce treatment; and (c) a controller having a processor and addressable memory and having a comparator adapted to difference ascorbate concentration derived from sensed Brix percentages and a concentration set point wherein the controller is adapted to transmit one or more ascorbate feed commands to a feed pump in response to the concentration difference. In some system embodiments, the controller may be further adapted to condition the concentration difference via a threshold hysteresis and a delay to generate the one or more ascorbate feed commands. In other system embodiments, the feed pump may be further adapted to output incremental amounts from an ascorbate source via a pulsed valve executing pulses proportionally cycled based on the difference value. In still other system embodiments, the feed pump may be further adapted to output ascorbate from an ascorbate source by executing pumping cycles proportionally based on the difference value.

Method and system embodiments of the present invention control the ascorbate concentration in produce treatments and particularly are exemplified in fresh cut fruit and vegetable treatments via the measured refractivity of the treatment solution. For example, a process for controlling ascorbate concentration of fresh produce treatment may comprise: (1) providing a fresh produce treatment comprised of water and ascorbic acid; (2) measuring the electrical conductivity of a sample comprised of the fresh produce treatment; (3) comparing an ascorbate concentration, derived from the measured electrical conductivity, with a control set point value to generate a difference value; and (4) if the difference value is above a threshold, then feeding ascorbate into the fresh produce treatment. In some embodiments of the process, the step of feeding ascorbate into the fresh produce treatment comprises feeding ascorbate in incremental amounts via a pulsed valve. In other embodiments of the process, the step of feeding ascorbate into the fresh produce treatment comprises feeding ascorbate in incremental amounts via a pulsed valve executing pulses proportionally cycled based on the difference value. In still other embodiments of the process, the step of feeding ascorbate into the fresh produce treatment comprises feeding ascorbate in via a pump having pumping cycles proportionally based on the difference value.

An exemplary system for controlling ascorbate concentration in a fresh produce treatment may comprise: (a) the fresh produce treatment comprised of water, calcium ions and ascorbic acid; (b) a subsystem comprising a sensor adapted to measure the electrical conductivity of the fresh produce treatment and a converter adapted to derive ascorbate concentration from measured electrical conductivity; and (c) a controller having a processor and addressable memory and having a comparator adapted to difference the ascorbate concentration derived from a sensed ascorbate concentration and a concentration set point wherein the controller is adapted to transmit one or more ascorbate feed commands to a feed pump in response to the concentration difference. In some system embodiments, the controller may be further adapted to condition the concentration difference via a threshold hysteresis and a delay to generate the one or more ascorbate feed commands. In other system embodiments, the feed pump may be further adapted to output incremental amounts from an ascorbate source via a pulsed valve executing pulses proportionally cycled based on the difference value. In still other system embodiments, the feed pump may be further adapted to output ascorbate from an ascorbate source by executing pumping cycles proportionally based on the difference value.

Method and system embodiments of the present invention control the ascorbate concentration in produce treatments and particularly are exemplified in fresh cut fruit and vegetable treatments via measured calcium ion concentrations. For example, a process for controlling calcium ascorbate concentration of fresh produce treatment may comprise: (1) providing a fresh produce treatment comprised of water, calcium ions and ascorbic acid; (2) measuring, via a calcium ion-specific sensor, a calcium ion concentration in a sample comprised of the fresh produce treatment; (3) comparing the measured calcium ion concentration with a control set point value to generate a difference value; and (4) if the difference value is above a threshold, then feeding calcium ascorbate into the fresh produce treatment. In some embodiments of the process, the step of feeding calcium ascorbate into the fresh produce treatment comprises feeding calcium ascorbate in incremental amounts via a pulsed valve. In other embodiments of the process, the step of feeding calcium ascorbate into the fresh produce treatment comprises feeding calcium ascorbate in incremental amounts via a pulsed valve executing pulses proportionally cycled based on the difference value. In still other embodiments of the process, the step of feeding calcium ascorbate into the fresh produce treatment comprises feeding calcium ascorbate in via a pump having pumping cycles proportionally based on the difference value.

An exemplary system for controlling calcium ascorbate concentration in a fresh produce treatment may comprise: (a) the fresh produce treatment comprised of water, calcium ions and ascorbic acid; (b) a calcium ion-specific electrode adapted to sense calcium ion concentrations in the fresh produce treatment; (c) a controller having a processor and addressable memory and having a comparator adapted to difference a sensed calcium ion concentration and a calcium ion concentration set point wherein the controller is adapted to transmit one or more calcium ascorbate feed commands to a feed pump in response to the concentration difference. In some system embodiments, the controller may be further adapted to condition the concentration difference via a threshold hysteresis and a delay to generate the one or more calcium ascorbate feed commands. In other system embodiments, the feed pump may be further adapted to output incremental amounts from a calcium ascorbate source via a pulsed valve executing pulses proportionally cycled based on the difference value. In still other system embodiments, the feed pump may be further adapted to output calcium ascorbate from a calcium ascorbate source by executing pumping cycles proportionally based on the difference value.

BRIEF DESCRIPTION OF THE DRAWINGS

Embodiments of the present invention are illustrated by way of example and not limitation in the figures of the accompanying drawings, and in which.

DETAILED DESCRIPTION OF EXEMPLARY EMBODIMENTS OF THE INVENTION

The several embodiments of an ascorbate monitoring and control system measure the refractive index as an indicator for the concentration of ascorbate in the fresh fruit or vegetable treatment which may be contained in a processed fresh produce treatment tank, a fresh produce processing tank or a processed produce dipping tank. A sensor subsystem is disclosed that accommodates continuous measurement and process conditions. The calibration relationship of refractive index to ascorbate concentration is disclosed. The several embodiments disclose a measurement analyzer that utilizes a linear calibration curve and expresses a refractive index on a brix percentage scale. By having a control law and reference or set point, system embodiments provide for an automatic feed and replenishment of ascorbate concentrate on demand, that is, when the measured concentration deviates from the reference point. For diagnostic or other forensic purposes, measured concentrations of ascorbate and/or feed pump commands may be recorded and stored.

The ascorbate automated monitoring and control system for fresh cut fruits and vegetables may be specialized for monitoring and maintaining the level of ascorbate in a solution via one or more means of determining and controlling the level ascorbate as sampled from the processing, of dip, tank. An operating principle of control system embodiments of the present invention includes in some embodiments the sensing of the refractive index of the process solution having a variation from pure or filtered water due in part to the control of ingredients in the solution, the measurement of refractivity may be correlated to the concentration of ascorbate. Generally, the ascorbate estimation and control system may be described as the combination of three primary processes: (1) the measurement process; (2) the sampling process; and (3) the control and injection process.

Figure 5:
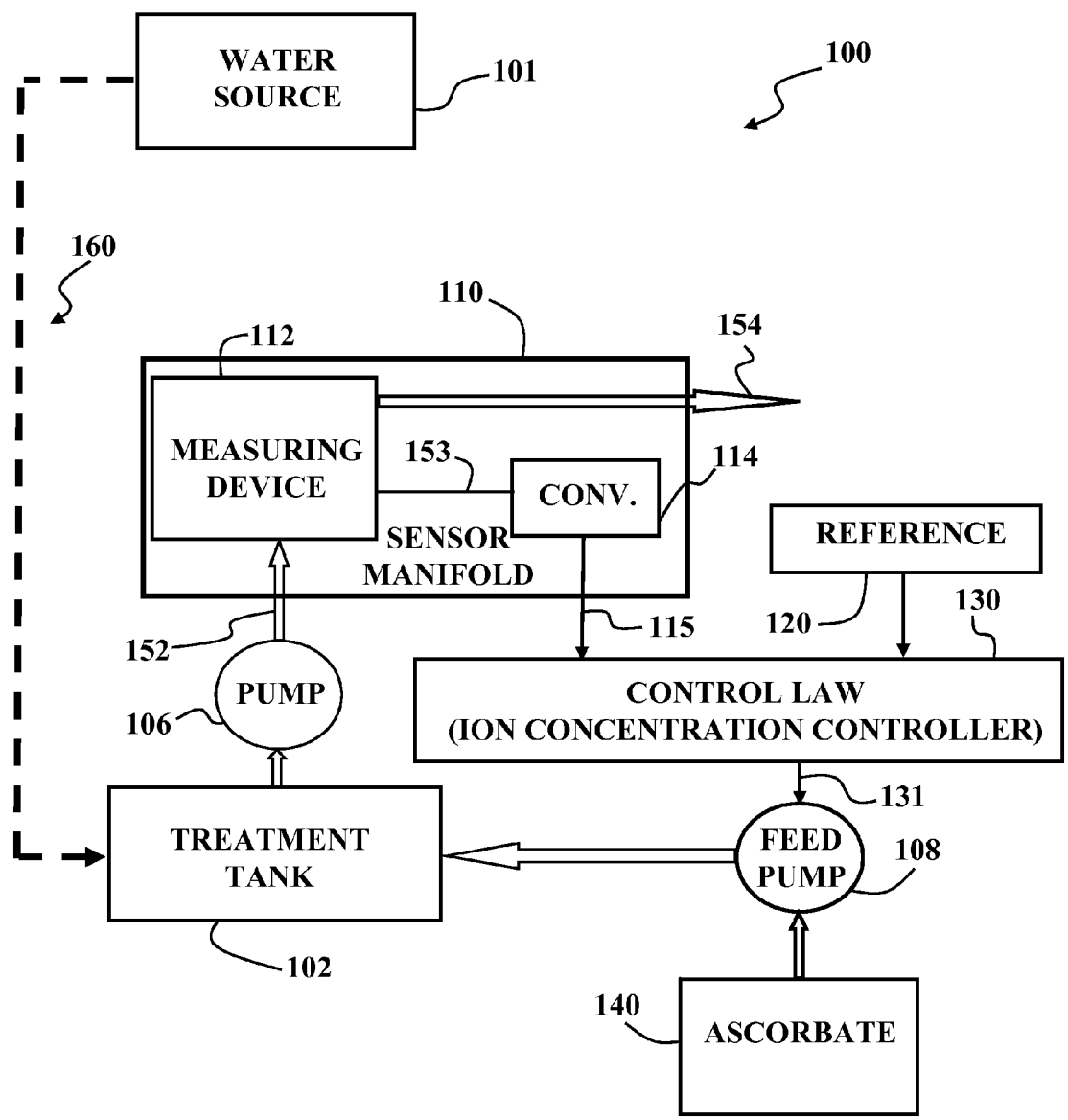
FIG. 5 is an exemplary top-level function lock diagram of a system embodiment of the present invention.

FIG. 5 illustrates an exemplary system embodiment 100 having a measurement analyzer 110 drawing water from both a water source 101 and a treatment tank 102 and a controller 130 outputting feed pump commands 131 based on an output of a measurement analyzer 110 and a reference value 120. The sensor manifold includes a refractometer, such as a Brix device 112, and a converter 114 that takes the Brix percentage output as 153 as its own input and in turn outputs 115 a derived ascobate concentration. Responsive to the control law output 131, the feed pump 108 dispenses ascorbate 140 into the treatment tank 102.

A first pump 108 may dispense ascorbate 140 to the treatment tank 102 having water provided 160 from a water source 101.

A second pump 106 may be employed to sample and provide 152 solution from the treatment tank to the measuring device 112 or an array of measuring devices. After the sampled solution 154 has been subjected to the one or more measuring devices, it may be returned to the treatment tank 102 or conveyed to a waste water reservoir.

Measurement Process via Refractometry

The measurement analyzer of the present invention may be built around refractometry and particularly may exploit a Brix meter. The refractive index is based upon the supposition that the refractive index in a vacuum is one, i.e., the absolute refractive index, and, for a particular medium passing light, the index varies with the wavelength of light and temperature of the medium. A standard for reflectivity may be represented by D where under the D-ray of natrium (r89 nm), the reflectivity index, N, of water at 20 degrees Celsius is 1.33299. The Brix percentage scale is based on the refractive index of water (nD=1.33299 as the reference, i.e., at a Brix percentage of 0%. The Brix percentage scale represents the weight of the sucrose expressed by percentage, e.g., the sucrose weight in grams contained in 100 grams of sucrose solution expressed as a percentage by weight. Therefore, this scale corresponds with the sucrose concentration. However, while sugar dissolves readily into water, most sample ingredients other than sugar are typically melted. The aggregate concentration of these ingredients is correlated with the Brix percentage, so this makes the Brix percentage scale a practical tool for measuring concentrations. Accordingly, any in-line, continuous monitoring, refractometer may be employed to detect the refractive index of a sample and output the Brix percentage value on a display. The refractive index of similar substances will vary with the temperature. When measuring the refractive index of a liquid by the refractometer, the measurement value carries with the sample temperature. By detecting the prism temperature, the indication value of the measurement is automatically corrected for temperature by a built-in-processor so that the indicated value is identical to the value measured at 20° C.

Sampling Pump

A pump is utilized to measure a representative sample of the process solution which may be of a piston, peristaltic, centrifugal or other type which may deliver a continuous sample.

Measurement Process via Electrical Conductivity

Figure 1:
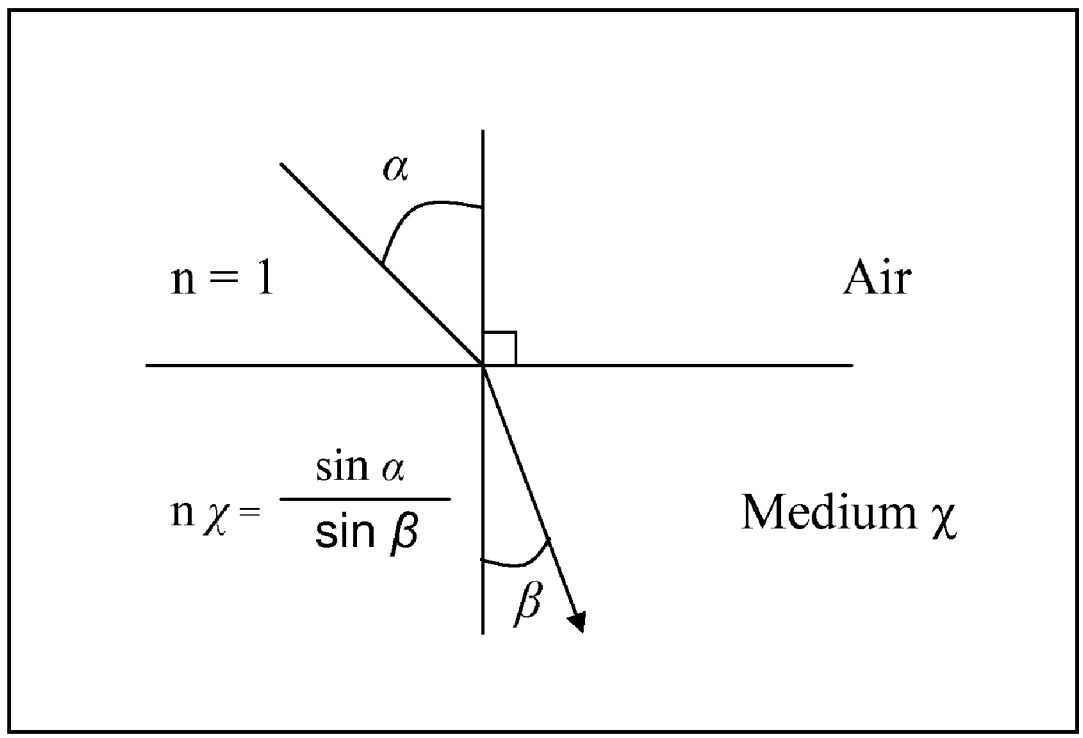
FIG. 1 is a graphic depiction of refraction.
Figure 2:
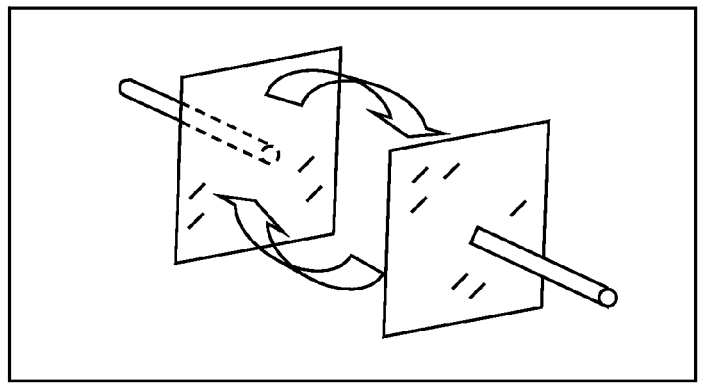
FIG. 2 is a depiction of an aspect of an exemplary instrument for measuring conductivity employing an anode and a cathode as two plates.
Figure 3A:
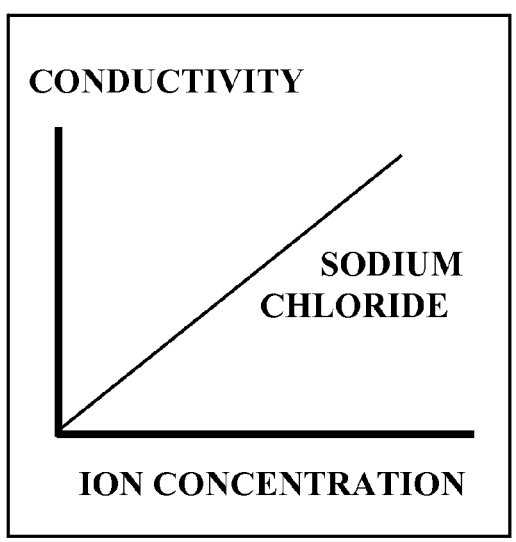
FIG. 3A is a graphical depiction of the relationship of the ion concentration of sodium chloride in solution with electrical conductivity.
Figure 3B:
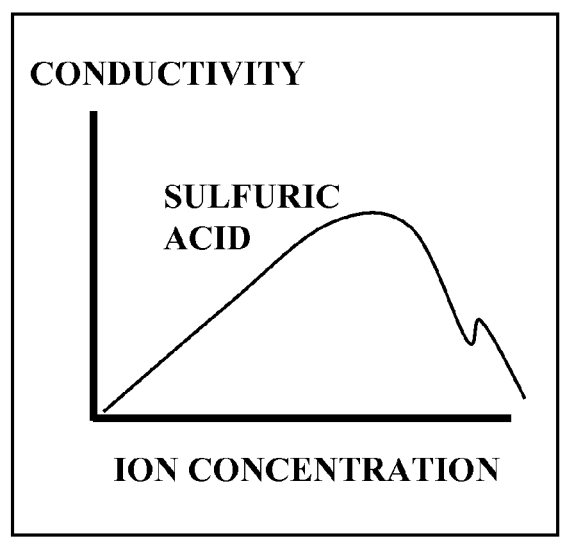
FIG. 3B is a graphical depiction of the relationship of the ion concentration of sulfuric acid in solution with electrical conductivity.

The basic unit of conductance is the siemen (S). Since cell geometry affects conductivity values, standardized measurements are expressed in specific conductivity units (S/cm) to compensate for variations in electrode dimensions. Specific conductivity (C) is simply the product of measured conductivity (G) and the electrode cell constant (L/A), where L is the length of the column of liquid between the electrodes and A is the area of the electrodes (FIG. 2).

$$C = G \times (L/A)$$

Conductivity Meter Calibration and Cell Maintenance

Conductivity meters and cells should be calibrated to a standard solution before being used. Select a standard that is closest to the conductivity of the solution to be measured. Polarized or fouled electrodes must be replatinized or cleaned to renew active surface of the cell. In most situations, hot water with a mild liquid detergent is an effective cleanser.

The conductivity of some common solutions is shown in Table 1 below.

TABLE 1

| Solution | Conductivity |
|---|---|
| Pure water | 0.055 μS/cm |
| Power plant boiler water | 1.0 μS/cm |
| Good city water | 50 μS/cm |
| Ocean water | 53 mS/cm |
| 31.0% HNO3 | 865 mS/cm |

Conductivity Temperature Compensation

Conductivity measurements are temperature dependent. The degree to which temperature affects conductivity varies from solution to solution and can be calculated using the following formula:

$$G_t = G_{teal}\{1 + \alpha(t - t_{cal})\}$$

where:
$G_t$=conductivity at any temperature t in ° C.
$G_{teal}$=conductivity at calibration temperature $t_{cal}$ in ° C.
α=temperature coefficient of solution at $t_{cal}$ in ° C.

Common alphas (α) are listed in Table 2 below. To determine the α of other solutions, one may measure conductivity at a range of temperatures and graph the change in conductivity versus the change in temperature and then divide the slope of the graph by $G_{teal}$ to get α.

TABLE 2

| Substance at 25° C. | Concentration | Alpha (α) |
|---|---|---|
| HCl | 10 wt % | 1.56 |
| KCl | 10 wt % | 1.88 |
| H$_2$SO$_4$ | 50 wt % | 1.93 |
| NaCl | 10 wt % | 2.14 |
| HF | 1.5 wt % | 7.20 |
| HNO$_3$ | 31 wt % | 31.0 |

Exemplary meters may be either fixed or adjustable automatic temperature compensation referenced to a standard temperature—usually 25° C. Most meters with fixed temperature compensation use an α of 2% per ° C. (the approximate α of NaCl solutions at 25° C.). Meters with adjustable temperature compensation let you adjust the alpha factor to more closely match the alpha factor of your solution.

Figure 4:
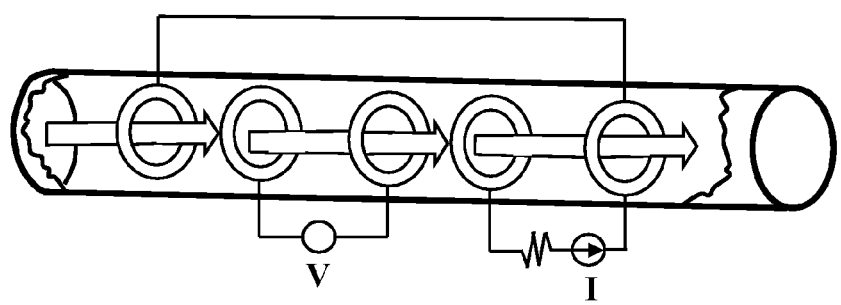
FIG. 4 is a depiction of an in-line placement of circuit elements of an electrical conductivity measuring device.

Conductivity Cells: Most conductivity meters have a two-electrode cell (FIGS. 2 and 4) available in either dip or flow-through styles. The electrode surface is usually platinum, titanium, gold-plated nickel, or graphite. Four-electrode cells use a reference voltage to compensate for any polarization or fouling of the electrode plates. The reference voltage ensures that measurements indicate actual conductivity independent of electrode condition, resulting in higher accuracy for measuring over wide ranges The measurement of the ions may be made either by a contacting or non-contacting conductivity sensor that is calibrated to the appropriate range of concentration, and interfaces with a conductivity instrument in order to display, via a calibrated scale, the measured value as a percentage of ascorbate. That is the conductivity instrument displays the value of ascorbate as a percentage concentration.

Sensor: The exemplary conductivity sensor is a non-contacting torroidal electrode that is specially constructed with coils encapsulated in a PVC housing so that coating sucrose and pectin byproducts of the process may not coat and affect the measurement accuracy. The non-contacting sensor creates an electric current and as the process solution passes through the sensor, a change in the strength of the current generated is proportional to the ion concentration. The encapsulated design remains protected and thereby minimizing maintenance downtime.

The sensor design selected for the trials had a non-contacting conductivity sensor that is not susceptible to clogging. The sensing element was encapsulated in a PVC housing and is protected from fouling failure. Accordingly, the sensor measures the solution conductivity and the ionic concentration, and the signal was then processed by a conductivity analytical process instrument.

Measurement/Sensor Manifold

A sensor manifold may be embodied to accept a continuous uninterrupted flow such as with a centrifugal or peristaltic pump, and due to the magnetic field generated by the sensor due to the two coils placed perpendicular to each other encapsulated in the PVC housing, a minimum two inch PVC Tee may be required to allow the field to remain stable for electrical conductivity assessment. The liquid stream is fed into the manifold from the ascorbate process dip tank through the bottom, passes through the sensor housing, and exits from the side of the Tee housing. The stream exits the electrode housing and may be returned back to the dip tank.

Sampling Pump

The single peristaltic pump or a centrifugal magnetic drive seal-less pump may be selected for some embodiments. The tubing of the peristaltic pump for suction and discharge for the trials was polyethylene one-quarter inch outer diameter (OD) and holds an approximate volume of 2.5 milliliter per foot (ml/ft) of tubing, and for the centrifugal pump, it is a one-half inch reinforced hose. The sampling pump selected preferably delivers the sample from the dip tank to the sensor in less than two minutes.

Measurement Based on Refractometry

Operation of the sensor portion of the exemplary system may include the following: (1) when power is supplied to the refractive index sensor, the Brix percentage measurement starts; (2) when the sample runs into the sample inlet unit and the prism surface is filled with the solution, the Brix percentage value may be displayed on a screen; (3) when the prism surface contacts air, it may signal such contact via a display such as the characters "LL.L"; (4) the instrument may then detect the temperature of the prism unit, and the Brix percentage indication values are automatically corrected for temperature to indicate values identical to the values measured at 20° C. when the sample temperature is in the range of 5 to 100° C.; (5) the temperature correction values for sucrose are selected due to the close refractive index of ascorbate and sucrose.

Measurement Based on Electrical Conductivity

A conductivity instrument is selected to process the signal from the sensor and displays the concentration of the ions, measured on a linear scale with the ability to enter a zero point and a reference point calibration. An electrode measurement system may be comprised of a contacting or non-contacting conductivity sensor which may be housed in an inline sensor manifold. An exemplary electrode-less toroidal conductivity sensor body containing a torroidal coil may be installed in a two inch PVC Tee.

When adjusting to the reference, confirm that the prism surface is clean. Before adjusting to the reference with distilled water, set the temperature correction factor to "1.00." Prudent steps in adjusting the reference include: (1) confirming that the sample inlet unit is properly connected to the piping; (2) running the distilled water or reference sample into the piping; (3) when the current Brix percentage is displayed, it may blink to allow for calibrations and during the blinking phase, incrementing an decrementing keys may be used to adjust the Brix percentage to be displayed as 0.0% for distilled water or to a known true value for a reference sample.

Ascorbate Concentration Control:

A proportional signal on a 4-20 milliamp (mA) scale may be processed by a programmable logic controller (PLC) or another control processor, which is programmed to display a concentration of ascorbate as a percentage of ascorbate. A control set point may be entered and the relay output from the controller will output 110 VAC on/off or pulse proportional control output below the set point to dispense a liquid stock concentrate of ascorbate. Alternatively a proportional analog signal output of a 4-20 mA from the controller may be used to determine the rate at which the ascorbate powder will be dropped into the flume.

Figure 6:
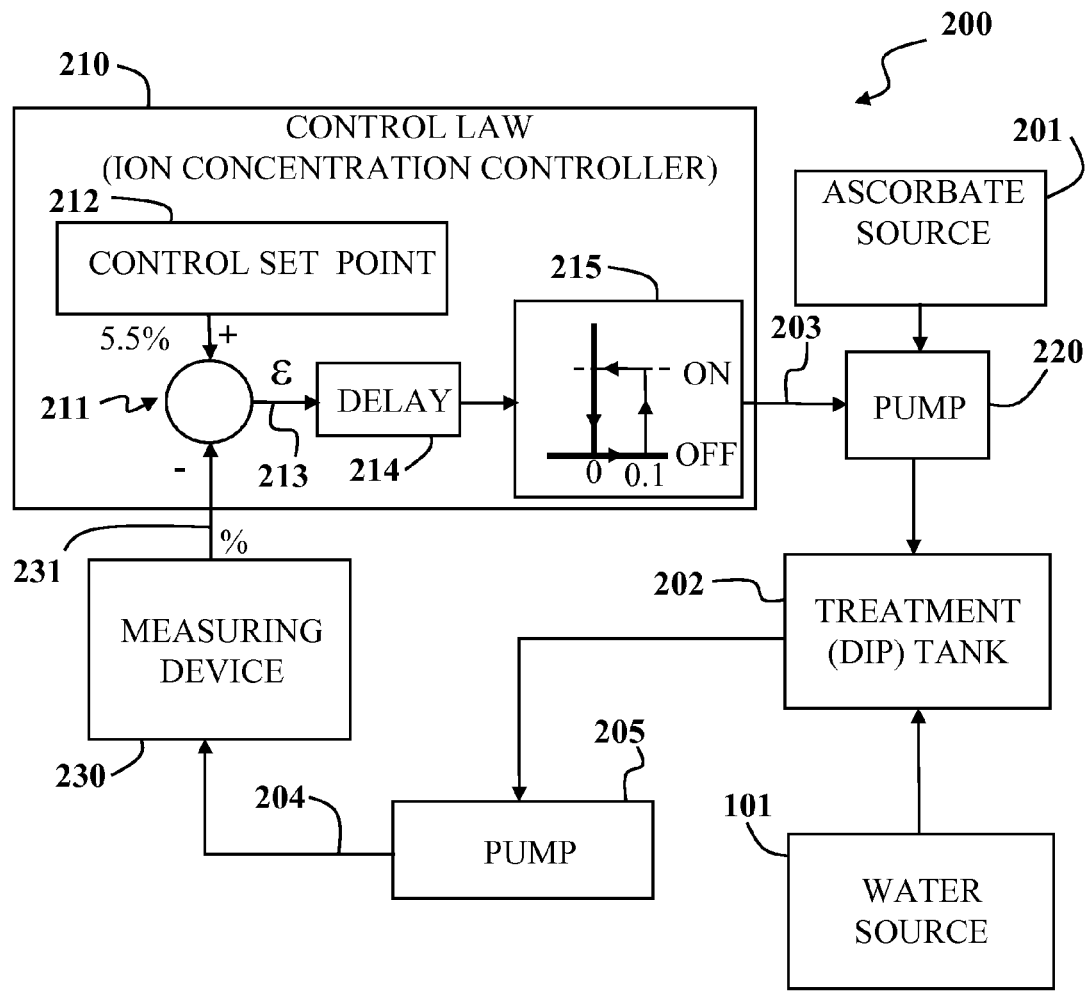
FIG. 6 is an exemplary top-level function lock diagram of a system embodiment of the present invention.

In exemplary configurations, there are three control laws by which an external dispensing device may be controlled by the instrument control panel: (1) ON/OFF control; (2) Pulse proportional control; and (3) Analog 4-20 mA control Exemplary ON/OFF Control:

FIG. 6 illustrates a system embodiment 200 having a pump 220, responsive to an effector signal 203 based on a control law 210 for feeding ascorbate 201 to a treatment tank 202 where the control law may have an ON/OFF relay rated at 5 amps/120 VAC that may be used to turn on and off an external pump 220, valve, feeder or any other 115 VAC powered external device. The feed rate of the pump 220 may not be modulated and as such, dispenses according to the pump 220 settings. The control law 210 may be embodied as one or more instructions of a general microcontroller, functioning as an ion concentration controller that may have a central processing unit (CPU) and addressable memory or may be embodied via a programmable logic controller (PLC). The control law in the example of FIG. 6 differences 211, from the control set point value 212, the ascorbate concentration 231 derived from the measuring device 230, such a Brix device if refractometric, or circuitry for measuring electrical conductivity, which is shown sampling a tapped flow 204 from the dip tank for an ascorbate concentration via a pump 205 pumping a sample flow from the dip tank sample 202. An error signal 213, E, resulting from the differencing 211 may be delayed via a time delay 214 of one or more sample cycles in order to accommodate the mixing time constant of the dip tank 202 as it receives ascorbate 201 via the pump 220. A threshold hysteresis 215 is shown where an effector signal outputs an "ON" value when the measured concentration falls below a set amount from the reference value.

An exemplary control set point may be 5.5% where the measurement scale is selected at 0 to 10%, and an adjustable hysteresis dead band set at 0.1% and a delay timer set to 5 seconds for the ON/OFF state change for the relay. When the reading falls below the set point 5.5% by the hysteresis value 0.1, i.e. at a concentration reading of 5.4%, the relay will turn ON after 5 seconds, turn ON the feed pump to add more calcium ascorbate and raise the concentration until the value reaches 5.5%, and then it will turn OFF. The change in concentration percentage value is slow and can take several minutes to change by a 0.1% concentration. Therefore the hysteresis and the delay timer and/or the inherent process time delay work to prevent the relay from chattering between the ON and OFF state. The on-off embodiment may be applied when the calcium ascorbate is in liquid form.

Exemplary Pulse Proportional Control:

The control relay described above may also be assigned as a pulse proportional relay. In this mode, the relay turns ON and OFF at a duty cycle frequency proportional to the extent to which the measured value deviates from the set point. The further the measured value is determined to be from the set point, the more frequently the relay will pulse, i.e., increase in the frequency of the duty cycle, and accordingly the pump 220 will inject the solution at a higher rate. The closer to the set point the measured value is determined to be, the slower the rate of pulsing, and the decreasing pulse rate decreases to practicably zero when the set point is reached by the determined measure value. The rate, i.e., cycles per second, of pulsing may be selected depending on the capability of the receiving pump or valve. For example, the range assigned to the pulse band is equivalent to the selected range of the instrument, i.e., 0 to 10%, but from the set point value to the point of maximum pulse rate value. For example, if the set point is 5.5%, the pulse output will begin as the reading falls below 5.5%, and reaches its maximum pulse rate at 0%.

Figure 7:
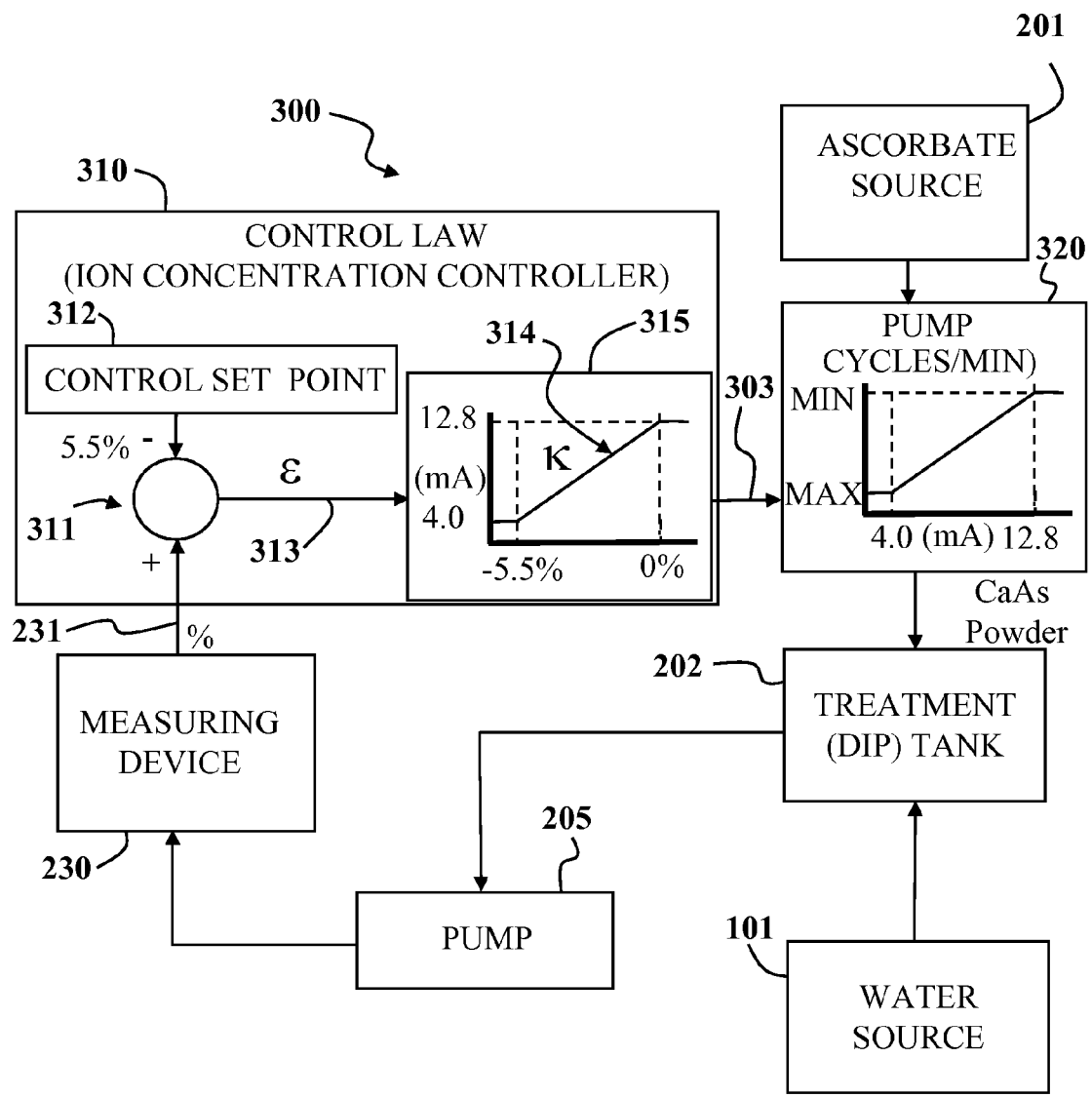
FIG. 7 is an exemplary top-level function lock diagram of a system embodiment of the present invention.

Exemplary Analog 4-20 mA Output:

FIG. 7 illustrates a system 300 having an analog output 303 that may be used to proportionally actuate a feed valve 320 or pump in proportion to the measured value 231. The control law 310 may be embodied in an ion concentration controller that is a microcomputer having addressable memory and adapted to execute one or more machine readable instructions to effect at least a proportional control or may be implemented in discrete steps via a PLC. An error signal 313, E, may be generated by differencing 311 the measured calcium ion concentration 231 from the control set point 312 and may be amplified into an effector signal 303 by applying a proportional gain 314, κ. The proportional gain may also have output signal limiting as shown by example in the gain-limiter block 315 of the control law 310. The feed pump 320 of FIG. 7 is shown to operate at a maximal frequency when the effector signal 303 is at its lowest value and to operate at a minimal frequency when the effector signal 303 is at its highest value. The analog signal embodiment may be applied when the calcium ascorbate source is in powder form.

Details of a preferred exemplary embodiment are as follows: a scale of 0 to 10% may be assigned equivalent to 4-20 mA output value, i.e., 4 mA equals 0% and 20 mA equals 10%. Differencing 4 mA from 20 mA yields 16 mA and provides for an exemplary definitional point of 10% which in turn allows for an exemplary slope of 1.6 mA per percentage point which sets the proportional gain. Accordingly in this example, an 8 mA range is allocated to accommodate a 5% concentration range. Since 4 mA is the beginning of the mA scale, the full range ends with at least 12 mA.

This output signal varies accordingly with changing values and may be used to proportion the feeder. For example, a set point value of 5.5% is 5.5×1.6+4=12.8 mA. Set the control pump input value of 0 cycles/min=to 12.8 mA, and 4 mA to max strokes/min. Thus, the further (lower) the measured value is from the set point, the faster the output pump will run, or the greater the output valve will open, thereby creating a proportional feed system.

13

Dispensing Pump:

While ascobate may be dispensed in a solid, e.g., sodium ascorbate or calcium ascorbate, or a liquid form as ascorbic acid in solution, the preferred dispensing of ascorbate is in a liquid form of 25% weight-per-volume (w/v), however other concentrations may be used. Since the exemplary control system is configured to dispense on demand, the higher the concentration, the less the dispensed volume is required to achieve the desired concentration in the dip tank. A peristaltic pump with variable speed adjustment may be selected at 85 gallons per day (GPD) capacity to allow for dip tank capacity variations.

Data Recording:

A data logger may be integrated into the instrument to interface with a scalable 4-20 mA output range signal proportional to a range of 1% to 10% of an ascorbate concentration.

Calibration for Refractometry

Calibrating the exemplary system for practicable operation may be described as calibrating within the sensor suite of instruments and calibrating the effector, particularly the ascorbate dispensing mechanism. System calibration may be effected via an exemplary adjustment to the reference. When adjusting to the reference, confirm that the prism surface is clean. Before adjusting to the reference with distilled water, set the temperature correction factor to "1.00." The following steps may be employed for calibrating the system for a particular Brix device: (1) confirming that the sample inlet unit is connected to the system piping; (2) running distilled water or a reference sample into the piping; (3) supplying power to the measurement and control system; and (4) placing the Brix device into a calibration mode.

Calibration for Electrical Conductivity

Exemplary Sensor Check and Calibration: An exemplary calibration procedure that requires two solutions may include the steps of: (1) Preparing an, at least 200 ml, apple wash water sample by cutting pieces of peeled apples in a container, adding fresh tap water, and allowing the admixture to soak, or sit, and mix for approximately one hour; (2) drawing, as zero calibration solution, a minimum of 200 ml as a sample of apple process wash water prepared in step (1) that, at this point should not contain any ascorbate anti-oxidant; (3) measuring the level of conductivity as a percentage value in the solution in order to use it as a zero calibration standard; (4) placing the sensor in-line and starting the running process solution from the treatment tank that contains ascorbate; (5) determining the ascorbate level in the process solution by titration and using the percentage value as the second standard; and (6) calibrating the second calibration standard as the reference point for the known value standard.

Ascorbate Measurements Based on Both Refractometry and Electrical Conductivity

In the ascorbate treatment process, certain errors may arise due to the progressive increase in sucrose and fructose levels in the water bath. These may also vary due to the type of commodity and variety of products that are processed. In order to automatically compensate for these progressive variations, a combination method of both conductivity and refractive index may be utilized as analytical techniques.

Refractive index measurements rely upon the change in the incident light in order to quantify the concentration of dissolved solids. Sugar variations follow a different slope of the relational line than ascorbate, and the combination of both follow a yet different slope. As the combined concentrations vary, the refractive index method is unable to clearly distinguish which of the two is causing the change. This limitation of the refractive index technique requires a correction method to clearly define the contribution of ascorbate alone.

The conductivity of an ascorbate anion is directly proportional to conductivity, and is a clear and distinct method of determining ascorbate concentration. The contribution of background ions in the make up water is negligible, and well below the margin of error. Sugars in general do not contribute to conductivity measurements since they do not contain free ionic charges. However conductivity alone is an insufficient measurement since it does not have measurement sensitivity in high ranges as compared to a refractive index, and has insufficient resolution to detect minor changes in ascorbate concentration.

A combination of both refractive index and conductivity may be applied to achieve both accuracy and sensitivity. The total refractive index is expressed as a percentage of total dissolved solids, i.e., sugars plus ascorbate on a slope calibrated to a combination of the two solutions. The total conductivity expressed as a percentage of ascorbate concentration is subtracted from the percentage of the refractive index on a brix scale, and the difference in measurement may be corrected by subtracting it from the refractive index brix percentage and expressing the corrected ascorbate measurement.

Figure 8:
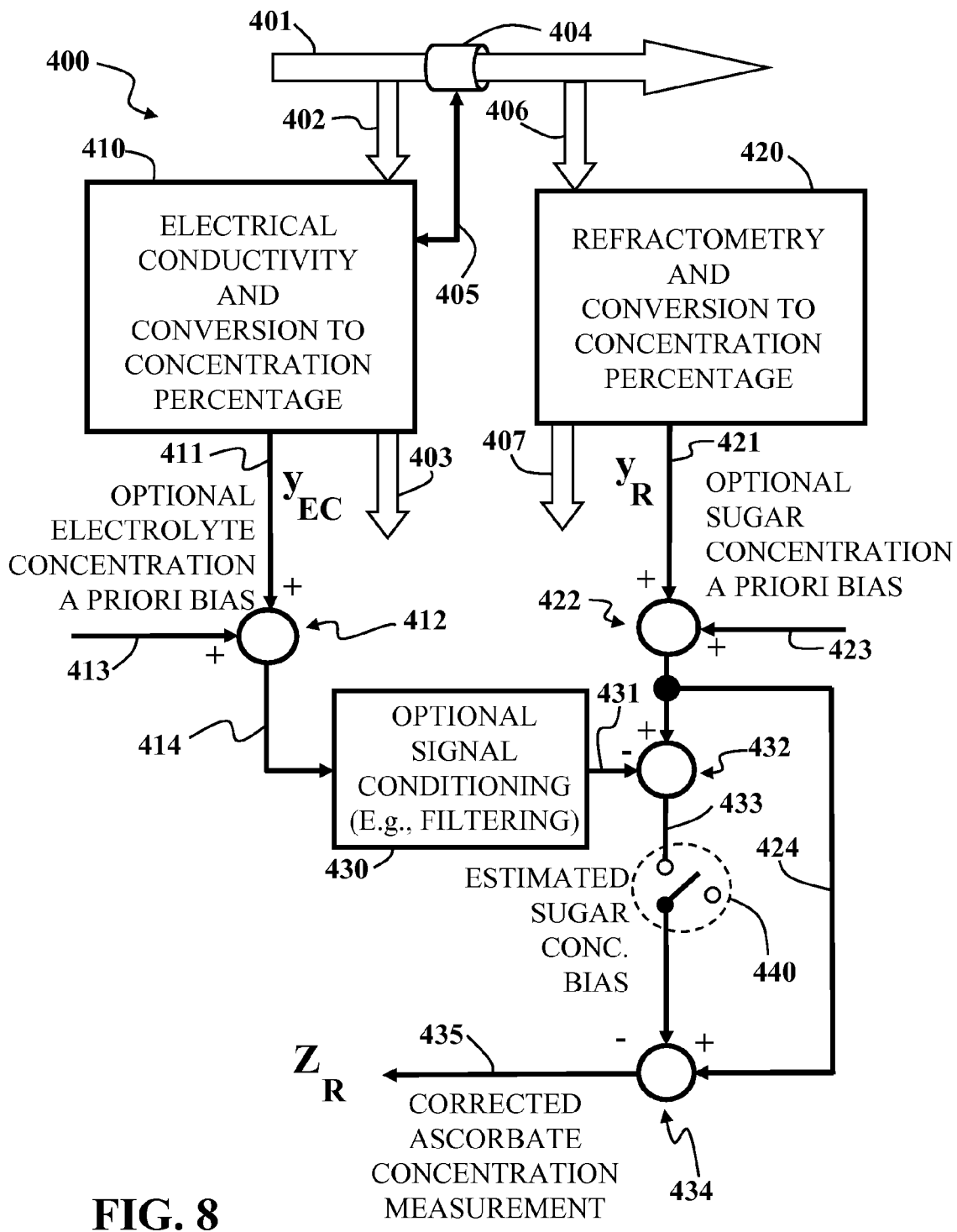
FIG. 8 is an exemplary top-level function lock diagram of an estimator of ascorbate concentration level in a sample based on both refractometry and measurements of electrical conductivity.

This adjusted measurement may then be used for a more accurate control mechanism. FIG. 8 illustrates a portion 400 of a system where a treatment solution 401 is tapped 402 and sampled by a circuit 410 that measures the electrical conductivity of the sample. The sample 403 may be returned to the treatment solution or sent to a waste water reservoir. In an alternative embodiment a portion 404 of the circuit 410 may be disposed about a conduit carrying the treatment solution and be placed in communication 405 with the remainder of the circuit measuring electrical conductivity or the portion 403 may be immersed in the treatment solution itself. The portion 400 of the system shown in FIG. 8 also illustrates the treatment solution 401 tapped 406 and sampled by a refractometer 420 or other prism-based device that derives concentrations in solutions based on the refractive index. The sample 407 may be returned to the treatment solution or sent to a waste water reservoir. The electrical conductivity may also have a conversion module that converts output voltages to representative percentage concentrations of electrolytes.

If the treatment solution is known via testing to contain electrolytes other than ascorbate and a corrected percentage concentration 414 is desired for control feedback, an optional electrolyte concentration bias may be established as an a priori bias 413 and combined 412 with the output 411 of the electrical conductivity measuring circuit 410. If the treatment solution is known via testing to contain solute, other than ascorbate, such as sucrose and/or fructose, and a corrected percentage concentration 424 is desired for control feedback, an optional refractometry-based concentration bias may be established as an a priori bias 423 and combined 422 with the output 421 of the refractometer 420. FIG. 8 illustrates an exemplary embodiment where the corrected percentage concentration 414 output from the electrical conductivity may be conditioned further, for example, by an electronic filter 430 such as a low-pass filter, which may reduce the higher frequency noise content in the signal 414 to one that may be used as a correcting bias 431.

The exemplary portion 400 of the system may combine 432 the unfiltered signal 414 or the filtered signal 431 representing the measured electrolyte concentration reflecting the concentration of ascorbic acid with the corrected percentage concentration 424 from the refractometry in order to generate a corrective bias value 433. If the corrective bias value 433 over time becomes larger that a threshold value that may represent the uncertainty range of measurements based on electrical conductivity, a switch 440 may close and allow for the combining 434 of the estimated sugar concentration bias 433 with the corrected percentage concentration 424 to generate a corrected ascorbate concentration measurement 435. Other embodiments for the exemplary portion 400 of the system include the outputs of the two measurement subsystems electronically weighted based on minimizing statistical variances and bias effects, and the weighted measurement combined to produce the corrected ascorbate measurement concentration.

The calibration relationship of calcium ions to calcium ascorbate concentration is disclosed by the exemplary embodiments below. The exemplary system embodiments have an in-line dilution system to exploit the measurement process within the sensor sensitivity and resolution. The several embodiments disclose a measurement analyzer that utilizes a semi-logarithmic calibration curve to adjust its output for subsequent action by the control effector. By having a control law and reference, e.g., a set point, system embodiments provide for an automatic feed and replenishment of calcium ascorbate concentrate "on demand," that is, when the measured concentration deviates from the reference point. For diagnostic or other forensic purposes, measured concentrations of calcium ascorbate and/or feed pump commands may be recorded and stored.

Ascorbate Concentration Control via Calcium Ion-Specific Measurement Devices

The operating principle of control system embodiments of the present invention is that by sensing the specific calcium (Ca++) ions in the process solution and the application of a control law to a calcium ascorbate source, the concentrations of ascorbate can be controlled according to the teachings of the instant specification. The sensing of calcium ions for an ascorbate control law is made practicable because, where the sole source of calcium ascorbate is controlled, the calcium ion concentration is directly proportional to the concentration of calcium ascorbate. So, in an exemplary application of the ascorbate control system to fresh cut fruits and vegetable, the calcium ascorbate automated monitoring and control system for fresh cut fruits and vegetables may be specialized for monitoring and maintaining the level of calcium ascorbate in solution.

Generally, the ascorbate estimation and control system may be described as the combination of three primary processes: (1) the measurement process; (2) the sampling process; and (3) the control and injection process.

Measurement Process

The measurement of the calcium ions may be made by an ion-specific electrode (ISE) that is calibrated to the appropriate range of concentration, and interfaces with an ion specific instrument in order to display, via a semi-logarithmic scale, the measured value as a percentage of calcium ascorbate. That is, the ISE instrument provides and may display the value of calcium ascorbate as percentage concentration.

Exemplary Sensor: The exemplary calcium ion specific sensor has an ion-specific membrane with a specially formulated reference electrolyte that allows a specific measurement of the free calcium ions in solution. The exemplary ion specific membrane is sensitive and could be saturated by the process solution concentration, interfering ion activity and high electron density. In order for a concentration to be in the preferred sensitivity range of the exemplary sensor, one may embody an inline dilution system in order to remain within a commercially practicable measurement resolution, as well as, to minimize the clogging rate of the reference junction of the sensor membrane, and thereby minimizing maintenance downtime.

A dilution rate of the calcium ascorbate process solution was determined in laboratory studies with numerous trials from sample solutions prepared having sliced apple wash bath as a base solution with varying amounts of calcium ascorbate. The sensor design selected for the trials had a refillable reference electrolyte with an easily flushable reference junction to clear clogging. The sensing element was PVC membrane specific and selective for Ca++ and may have been formatted either integrally or in combination with the reference electrode or may have been embodied as a separate mono electrode. Accordingly, the sensor measured the Ca++ ion concentration and the signal was then processed by an ion specific instrument.

Figure 9:
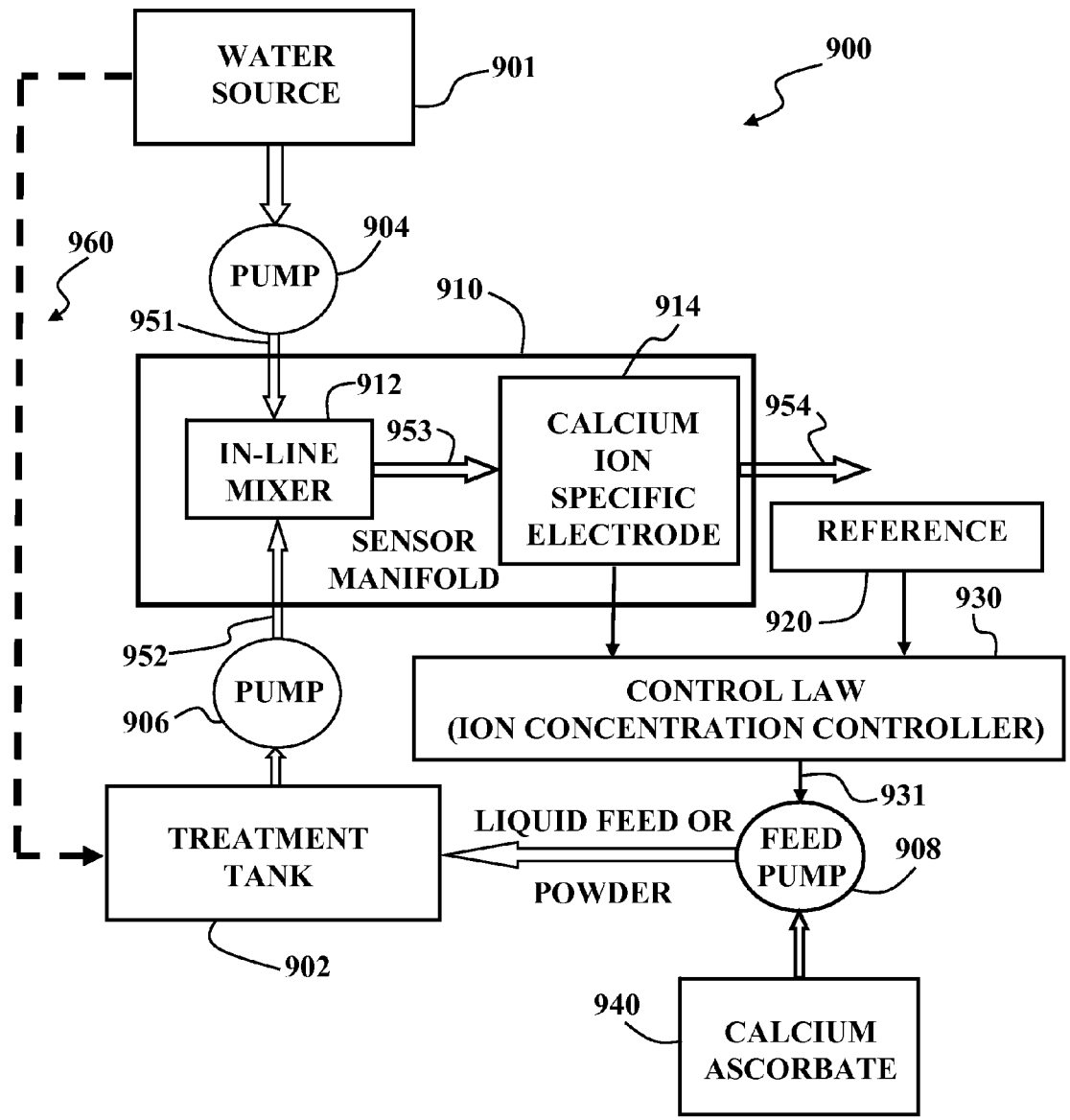
FIG. 9 is an exemplary top-level function lock diagram of a system embodiment of the present invention.

FIG. 9 illustrates an exemplary system embodiment 900 having a sensor manifold 910 drawing water from both a water source 901 and a treatment tank 902 and a controller 930 outputting feed pump commands 931 based on the output of a calcium ion-specific electrode 914 and a reference value 920. The sensor manifold includes the calcium ion-specific electrode and an in-line mixer 912 that combines water drawn from the water source via a first pump 904 with water drawn from the treatment tank 902 via a second pump 906. Responsive to the control law output 931, the feed pump 908 dispenses calcium acscorbate 940 into the treatment tank 902 and the calcium ascorbate may be dispensed in liquid or powder form.

Measurement/Sensor Manifold: The sensor manifold 910 may be embodied to accept two liquid streams and may preferably have a continuous uninterrupted flow, such as with a peristaltic pump. The water source for the calcium ascorbate process treatment tank, or dip tank, may also be the water source for the first liquid stream 951 into the manifold as shown in FIG. 9 as an optional flow path 960. A second liquid stream 952 is shown feeding into the manifold from the calcium ascorbate process dip tank. The two streams are shown feeding into a common line and the confluence is then passed through a static in-line mixer 912 in order to ensure a homogeneous stream. The combined stream 953 is shown as then passing into an electrode flow cell chamber where the sensing electrode is located so that it may sense the Ca++ concentration. The combined stream 954 is shown exiting the electrode housing and may be returned back to the dip tank or may be sent to waste for recycling outside of the estimation and control system environment.

A calcium electrode measurement system may be comprised of a reference electrode and a calcium Ion Specific Electrode (ISE). These two electrodes may be separated or may be integrated as a single combination electrode.

An exemplary calcium ISE includes an electrode body containing an ion exchanger in a sensing module that contains a liquid internal fill solution in contact with a gelled organophilic membrane containing a calcium selective ion exchanger. An electrode potential develops across the membrane when the membrane is in contact with a calcium solution. Measurement of this potential against a constant reference potential with a digital millivolt (mV) or ion specific meter depends on the level of free calcium ions in solution, and corresponds to the measured potential as described by the Nernst equation:

$$E = E_0 + S\,\log X;$$

where:
 E=measured electrode potential;
 $E_0$=reference potential (a constant);

S=electrode slope (~25 mV/decade); and

X=level of calcium ions in solution.

The activity X represents the effective concentration of the ions in solution. Total calcium concentration, $C_t$, includes a concentration of free calcium ions, $C_f$, plus a concentration of complex calcium ions, $C_b$. Since the calcium electrode only responds to the free ion, the free ion concentration, $C_f$, may be represented as:

$$C_f = C_t - C_b.$$

The activity, X, may be related to the free ion concentration, $C_f$, by the activity coefficient γ by:

$$X = \gamma C_f.$$

Activity coefficients vary, and can depend on the total ionic strength, I, where the total ionic strength may be defined as:

$$I = \tfrac{1}{2} \Sigma_x C_x Z_x^2$$

where:

$C_x$=even concentration of ion X;

$Z_x$=charge on ion X; and

Σ=sum of all types of ions in the solution.

In the case of high and constant ionic strength relative to the sensed ion concentration, the activity coefficient, γ, is constant and the activity, X, is directly proportional to the concentration.

Reference Electrode:

When two solutions of different compositions are brought in to contact with one another, liquid junction potentials arise. Millivolt (mV) potentials occur from the inter-diffusion of ions into the solutions. Electrode charges will be carried unequally across the solution boundary resulting in a potential difference between the two solutions, since the ions diffuse at different rates. It is important that the potential be the same when the reference is in the standardizing solution and the sample, otherwise a change in liquid junction potential will appear as an error in the measured electrode potential.

The composition of the liquid junction filling solution in the reference electrode affects the speed with which the positive and negative ions in the filling solution diffuse in to the sample and should be equitransferent. No junction potential will result if the positive and negative charge carried into the sample is equal.

The Sampling Process

Sampling Pump: The exemplary single peristaltic pump has a dual head with independent flow rate adjustment. The peristaltic pumps may be a dual head or two single head pumps and may also be fixed or variable speed, for example those capable of delivering a 1:10 ratio of calcium ascorbate to water. The tubing of the peristaltic pump for suction and discharge for the trials is polyethylene one-quarter inch outer diameter (OD) and holds an approx. volume of 2.5 ml/ft of tubing. The sampling pump selected preferably delivers the sample from the dip tank to the sensor in less than 20 minutes.

Measurement and Control

An ion specific measurement instrument 114 is shown having been selected to process the signal from the sensor and displays the concentration of the specific ion, that in this example is measured on a semi-logarithmic scale separated by at least 14 mV to 25 mV per decade change in concentration of the specific Ca++ divalent cation. A control set point as a reference 120 may be entered and the output 131 from the controller in some embodiments will output a 110 VAC on/off or a pulse proportional control output below the set point in order to dispense, via the feed pump 108, a liquid stock concentrate of calcium ascorbate. Alternatively a proportional analog signal output of a 4-20 mA from the ion concentration controller may be used to determine the effect rate, at the feed pump 108, at which the calcium ascorbate powder will be dropped into the flume.

The Control and Injection Process

Figure 10:
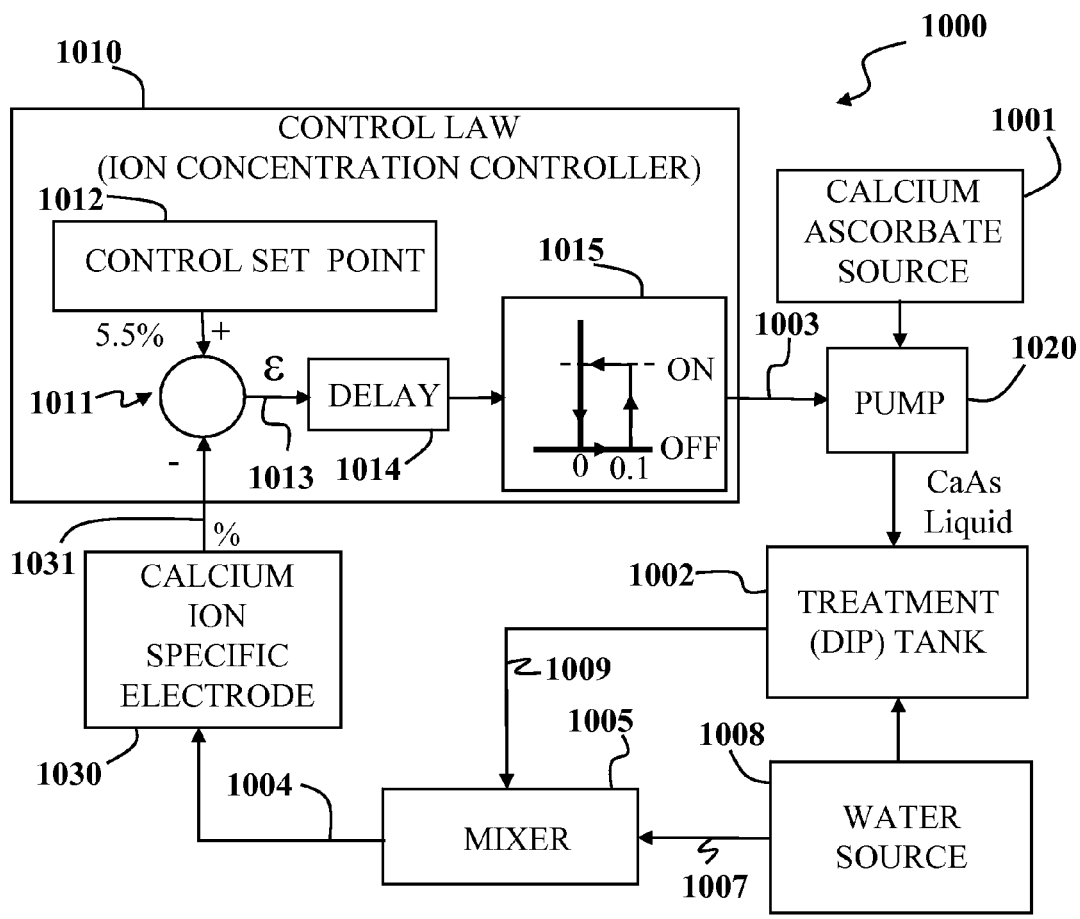
FIG. 10 is an exemplary top-level function lock diagram of a system embodiment of the present invention.

Control: In an exemplary configuration, there are three control laws by which an external dispensing device may be controlled by the instrument control panel: (1) ON/OFF control; (2) Pulse proportional control; and (3) Analog 4-20 mA control Exemplary ON/OFF Control FIG. 10 illustrates a system embodiment 1000 having a pump 1020, responsive to an effector signal 1003 based on a control law 1010 for feeding calcium ascorbate 1001 to a treatment tank 1002 where the control law may have an ON/OFF relay rated at 5 amps/120 VAC that may be used to turn on and off an external pump 1020, valve, feeder or any other 115 VAC powered external device. The feed rate of the pump 1020 may not be modulated and as such, dispenses according to the pump 1020 settings. The control law 1010 may be embodied as one or more instructions of a general microcontroller, functioning as an ion concentration controller, that may have a central processing unit (CPU) and addressable memory or may be embodied via a programmable logic controller (PLC). The control law in the example of FIG. 10 differences 1011, from the control set point value 1012, the calcium ion concentration 1031 derived from the calcium ion-specific electrode 1030 which is shown sampling a confluence 1004 from the dip tank for a calcium ion concentration via a mixer 1005 that mixes the dip tank sample 1007, 1009 with a water source 1008. An error signal 1013, ε, resulting from the differencing 1011 may be delayed via time delay 1014 of one or more sample cycles in order to accommodate the mixing time constant of the dip tank 1002 as it receives calcium ascorbate 1001 via the pump 1020. A threshold hysteresis 1015 is shown where an effector signal outputs an "ON" value when the measured concentration falls below a set amount from the reference value.

An exemplary control set point may be 5.5% where the measurement scale is selected at 0 to 10%, and an adjustable hysteresis dead band set at 0.1% and a delay timer set to 5 seconds for the ON/OFF state change for the relay. When the reading falls below the set point 5.5% by the hysteresis value 0.1, i.e. at a concentration reading of 5.4%, the relay will turn ON after 5 seconds, turn ON the feed pump to add more calcium ascorbate and raise the concentration until the value reaches 5.5%, and then it will turn OFF. The change in concentration percentage value is slow and can take several minutes to change by a 0.1% concentration. Therefore the hysteresis and the delay timer and/or the inherent process time delay work to prevent the relay from chattering between the ON and OFF state. The on-off embodiment may be applied when the calcium ascorbate is in liquid form.

Exemplary Pulse Proportional Control

The control relay described above may also be assigned as a pulse proportional relay. In this mode, the relay turns ON and OFF at a duty cycle frequency proportional to the extent to which the measured value deviates from the set point. The further the measured value is determined to be from the set point, the more frequently the relay will pulse, i.e., increase in the frequency of the duty cycle, and accordingly the pump 1020 will inject the solution at a higher rate. The closer to the set point the measured value is determined to be, the slower the rate of pulsing, and the decreasing pulse rate decreases to practicably zero when the set point is reached by the determined measure value. The rate, i.e., cycles per second, of pulsing may be selected depending on the capability of the receiving pump or valve. For example, the range assigned to the pulse band is equivalent to the selected range of the instrument, i.e., 0 to 10%, but from the set point value to the point of maximum pulse rate value. For example, if the set point is 5.5%, the pulse output will begin as the reading falls below 5.5%, and reaches its maximum pulse rate at 0%.

Figure 11:
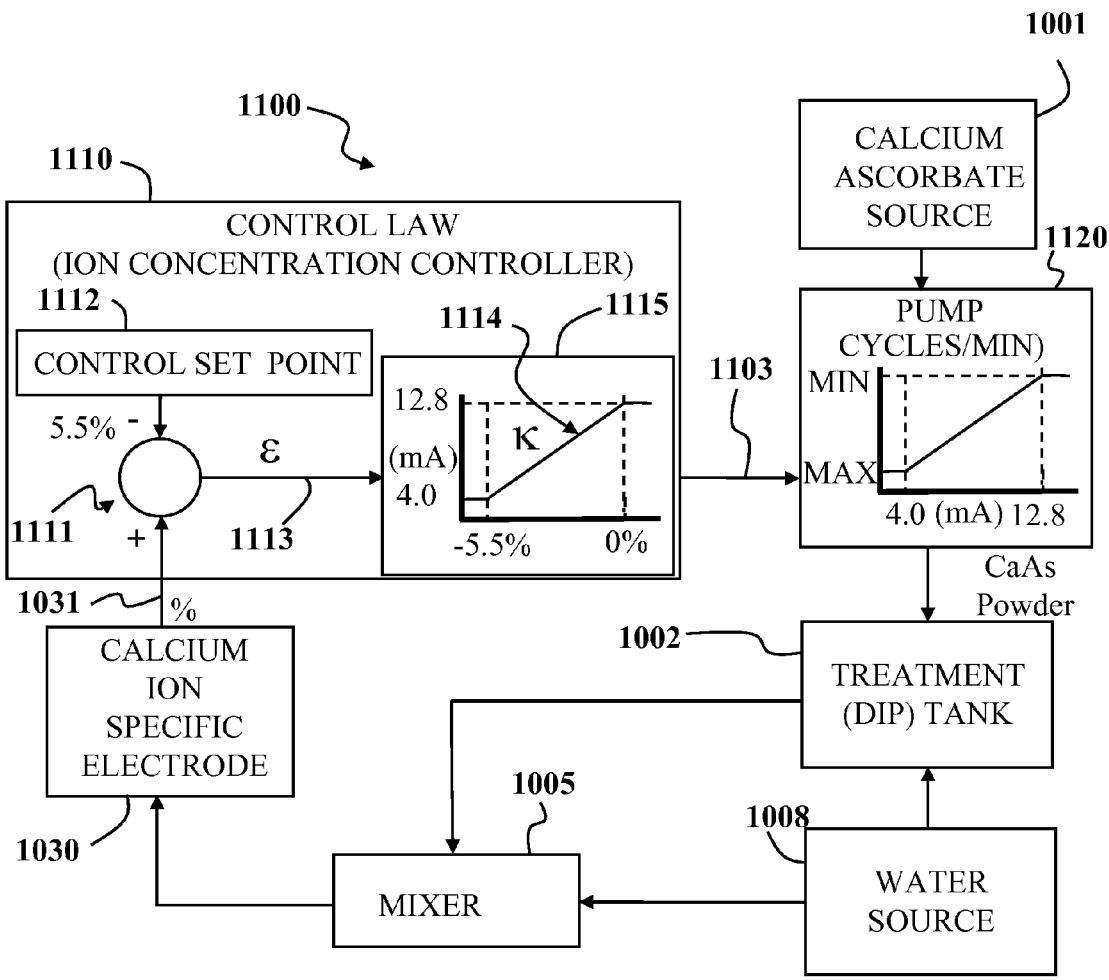
FIG. 11 is an exemplary top-level function lock diagram of a system embodiment of the present invention.

Exemplary Analog 4-20 mA Output:

FIG. 11 illustrates a system 1100 having an analog output 1103 that may be used to proportionally actuate a feed valve 1120 or pump in proportion to the measured value 1031. The control law 1110 may be embodied in an ion concentration controller that is a microcomputer having addressable memory and adapted to execute one or more machine readable instructions to effect at least a proportional control or may be implemented in discrete steps via a PLC. An error signal 1113, $\epsilon$, may be generated by differencing 1111 the measured calcium ion concentration 1031 from the control set point 1112 and may be amplified into an effector signal 1103 by applying a proportional gain 1114, $\kappa$. The proportional gain may also have output signal limiting as shown by example in the gain-limiter block 1115 of the control law 1110. The feed pump 1120 of FIG. 11 is shown to operate at a maximal frequency when the effector signal 1103 is at its lowest value and to operate at a minimal frequency when the effector signal 1103 is at its highest value. The analog signal embodiment may be applied when the calcium ascorbate source is in powder form.

Details of a preferred exemplary embodiment are as follows: a scale of 0 to 10% may be assigned equivalent to a 4-20 mA output value, i.e., 4 mA equals 0% and 20 mA equals 10%. Differencing 4 mA from 20 mA yields 16 mA and provides for an exemplary definitional point of 10% which in turn allows for an exemplary slope of 1.6 mA % which sets the proportional gain. Accordingly in this example, an 8 mA range is allocated to accommodate a 5% concentration range. Since 4 mA is the beginning of the mA scale, the full range ends with at least 12 mA.

This output signal varies accordingly with changing values and may be used to proportion the feeder. For example, a set point value of 5.5% is 5.5×1.6+4=12.8 mA. Set the control pump input value of 0 cycles/min=to 12.8 mA, and 4 mA to max strokes/min. Thus, the further (lower) the measured value is from the set point, the faster the output pump will run, or the greater the output valve will open, thereby creating a proportional feed system.

Dispensing Pump:

While calcium ascorbate may be dispensed in a solid or a liquid form, the preferred dispensing of calcium ascorbate is in a liquid form of 50% w/v, however other concentrations may be used. Since the control system is designed to dispense on demand, the higher the concentration, the less the dispensed volume is required to achieve the desired concentration in the dip tank. A peristaltic pump with variable speed adjustment may be selected at 85 GPD capacity to allow for dip tank capacity variations.

Data Recording:

A data logger may be integrated into the instrument to interface with a scalable 4-20 mA output range signal proportional to a range of 1% to 10% of a calcium ascorbate concentration.

Sensor Calibration

Calibrating the exemplary system for practicable operation may be described as calibrating within the sensor suite of instruments and calibrating the effector, particularly the calcium ascorbate dispensing mechanism.

An exemplary sensor check, or calibration, may be disclosed for apple processing as follows: (1) one may prepare a 100 ml solution of 1% and 10% calcium ascorbate in apple process water: (a) in order to prepare a 1% solution, take 100 ml of water in which sliced apples have been washed, and where the water does not contain any calcium ascorbate and then add 1 gram of powder calcium ascorbate and stir until dissolved; (b) in order to prepare a 10% solution, take 100 ml of water in which sliced apples have been washed, and where the water does not contain any calcium ascorbate and add 10 grams of powder calcium ascorbate and stir until dissolved; (2) one may prepare a 100 ml solution of diluted 1:10 of 1% and 10% calcium ascorbate in water that may be added to the contents of the dip tank: (a) in order to prepare a 1:10 dilution of 1% solution, one may take 90 ml of water and 10 ml of the 1% solution (prepared in the preceding step of step (1)(a)), (b) in order to prepare a 1:10 dilution of 10% solution, one may take 90 ml of water and 10 ml of the 10% solution (prepared in the preceding step of step (1)(b)); (3) one may then connect the calcium electrode to the ion specific meter and place the meter into a 0.1 mV resolution mode; (4) one may measure the 1% solution prepared in step (2)(a) and note the mV value and measure the mV value of the 10% solution (prepared in the preceding step of step (2)(b)); and (5) one may note that the slope of the electrode is the value difference between the two samples separated by a one decade concentration, i.e., 1% and 10% and that the slope should be between 14 and 25 mV.

Alternatively, a second exemplary sensor calibration method relying on two liquid solutions may be used for cut and peeled apple processing: (1) draw a minimum 200 ml sample of apple process wash water containing the ascorbate anti-oxidant; (2) measure the level of ascorbate in the solution by titration where the sample preferably has an ascorbate level of at least 5% (and is typically a level that may be shared by the second step of the previous exemplary method of calibration); (3) prepare at least a 200 ml apple wash water sample by cutting pieces of some peeled apples in a container and adding fresh tap water and allow about one hour for soaking and mixing; (4) draw 90 ml of the sample prepared in step (3) and draw 10 ml from standard 2, i.e., the solution prepared at step two of the preceding process, in order to prepare standard 1 at ⅟₁₀th the concentration of standard 2 (by noting the two values: if standard 2 is =5%, then standard 1 is ⅟₁₀th of standard 2 and is =0.5%); and (5) one may then connect the calcium electrode to the ion specific meter and place the meter into a 0.1 mV resolution mode; one may measure the standard no. 1 solution prepared in step 4 and note the mV value and measure the mV value of the standard no. 2 solution (prepared in the preceding method's step (2)) one may note that the slope of the electrode is the value difference between the two samples separated by a one decade concentration, i.e., 0.5% and 5% and that the slope should be between 14 and 25 mV.

Control System Calibration

An exemplary control system calibration may be described as follows: (1) With the system in operational configuration with the manifold, and sampling pumps connected and electrode placed in the manifold perform an inline calibration; (2) Connect the suction tube of the sampling pump to the 1% calcium ascorbate standard solution prepared in (1)(a) and run the 1:10 inline water dilution pump. Wait until the sample reaches the electrode and select the calibration mode on the instrument: (a) Select the two point calibration; (b) Select 10 decade value; (c) Value of first calibration point is 1%; and (d) After reading is stabilized, accept the first measurement; (3) Move the suction tube of the sampling pump to the 10% calcium ascorbate standard solution prepared in (1)(b) and run the 1:10 inline water dilution pump. Wait until the sample reaches the electrode: (a) Value of second calibration point is 10%; and (b) After the reading is stabilized, accept the second measurement; and (4) Re-connect the suction tubing to the process tank.

Ascorbate Measurements Based on Refractometry, Electrical Conductivity and Calcium Ions In the measurement of ascorbate solutions in process applications, there may be three analytical techniques applied in order to determine the percentage concentration of ascorbate ions. Complexities that arise in a continuous process due to the dynamically changing nature of the ascorbate dip solution include variations in sugar content of commodity types, product variety, and the formulation of the ascorbate additive and its derivatives.

For processing using calcium ascorbate, deriving ascorbate concentration percentages indirectly based on a calcium ion-specific electrode is a technique that, as described above, may be effective in correlating the measured calcium ion concentration to the concentration of ascorbate percentage. However, inaccuracies may arise if different formulations and additives within the ascorbate are introduced that may be calcium or other interfering ion bases. For example, the calcium ascorbate formulation may at times also contain calcium carbonate, which can throw off the correlation between calcium ions and ascorbate. Other formulations of ascorbate, such as sodium ascorbate, may be used where calcium ions are not present at all. In such instances, the calcium ion specific measurement technique is limited.

Figure 12:
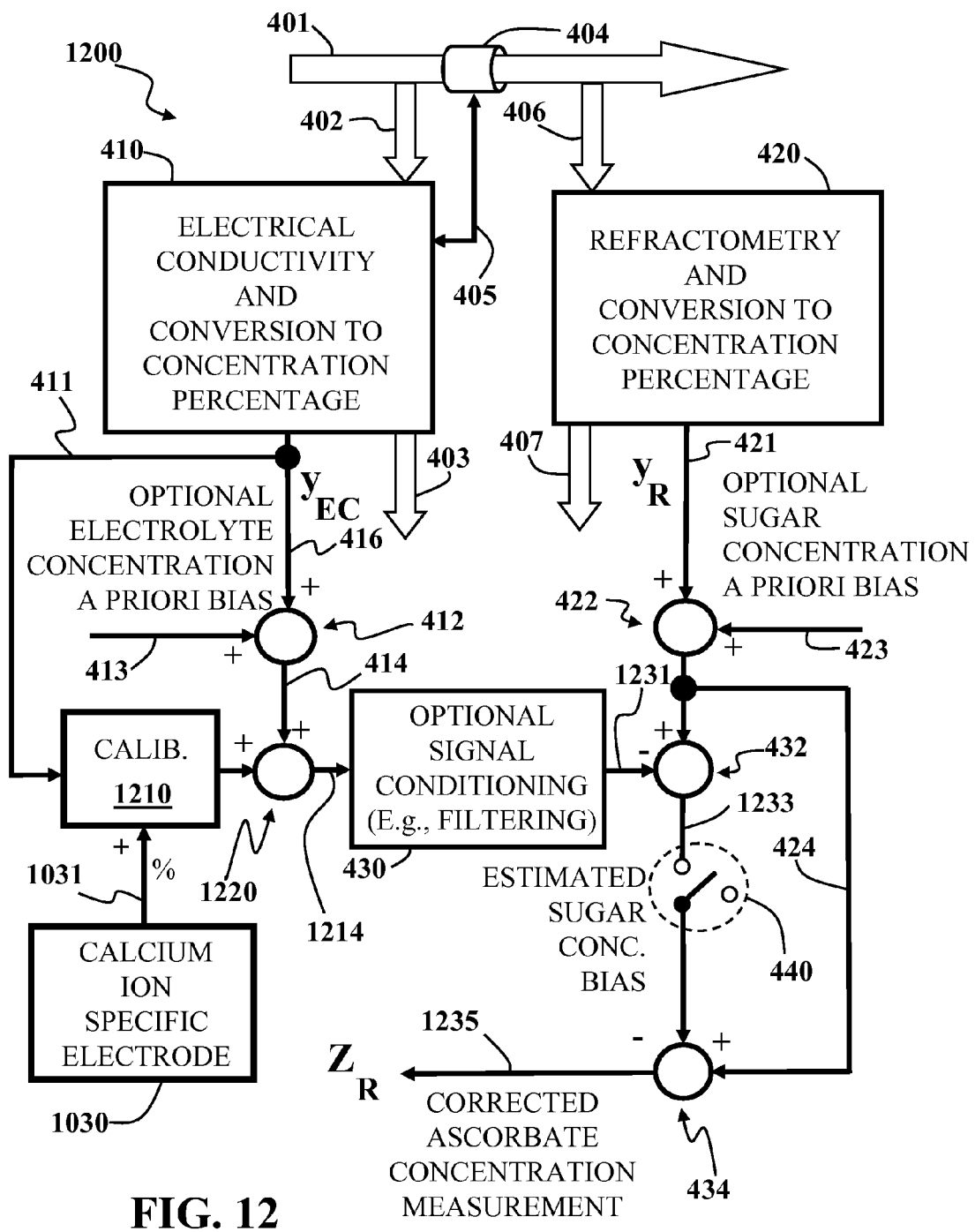
FIG. 12 is an exemplary top-level function lock diagram of an estimator of ascorbate concentration level in a sample based on refractometry, measurements of electrical conductivity, and measurements from a calcium ion-specific electrode.

A combination of all three analytical techniques of deriving ascorbate percentages: calcium ion-specific measurement, refractive index; and conductivity may be applied to achieve greater reliability, accuracy and sensitivity. The total refractive index is expressed as a percentage of total dissolved solids, i.e., sugars plus ascorbate on a slope calibrated to a combination of the two solutions. Referring to FIG. 12, the total conductivity expressed as a percentage of ascorbate concentration 1214 may be subtracted from the percentage of refractive index on a brix scale 424, and the difference in measurement may be corrected by subtracting 434 it from the refractive index brix percentage 424 and outputting the corrected ascorbate measurement 1235. In the case of ascorbate solutions where calcium ascorbate derivative is utilized, the calcium ion-specific sensor 1030 (FIG. 10) may be used as a comparative reference to verify accuracy of the device measuring electrical conductiviey, and a correction factor may be programmed, as a calibrating value 1210, to adjust 1220 the slope of the conductivity measurement 414, which then accounts for all the ions and is corrected specifically for calcium as the ion species of choice. Then the comparative value of refractive index 424 is used corrected for by the calcium adjusted conductivity measurement 1233 in order to provide the best accuracy in the face of rising sugars and complex ionic compositions.

This adjusted measurement 1235 may then be used for a more accurate control mechanism. FIG. 12 illustrates a portion 1200 of a system where a treatment solution 401 is tapped 402 and sampled by a circuit 410 that measures the electrical conductivity of the sample. The sample 403 may be returned to the treatment solution or sent to a waste water reservoir. In an alternative embodiment a portion 404 of the circuit 410 may be disposed about a conduit carrying the treatment solution and be placed in communication 405 with the remainder of the circuit measuring electrical conductivity or the portion 403 may be immersed in the treatment solution itself. The portion 400 of the system shown in FIG. 12 also illustrates the treatment solution 401 tapped 406 and sampled by a refractometer 420 or other prism-based device that derives concentrations in solutions based on the refractive index. The sample 407 may be returned to the treatment solution or sent to a waste water reservoir. The electrical conductivity may also have a conversion module that converts output voltages to representative percentage concentrations of electrolytes.

If the treatment solution is known via testing to contain electrolytes other than ascorbate and a corrected percentage concentration 414 is desired for control feedback, an optional electrolyte concentration bias may be established as an a priori bias 413 and combined 412 with the output 411,416 of the electrical conductivity measuring circuit 410. If the treatment solution is known via testing to contain solute, other than ascorbate, such as sucrose and/or fructose, and a corrected percentage concentration 424 is desired for control feedback, an optional refractometry-based concentration bias may be established as an a priori bias 423 and combined 422 with the output 421 of the refractometer 420. FIG. 12 also illustrates an exemplary embodiment where the corrected percentage concentration 1214 output from the electrical conductivity may be conditioned further, for example, by an electronic filter such as a low-pass filter, which may reduce the higher frequency noise content in the signal 414 to one that may be used as a correcting bias 1231.

The exemplary portion 1200 of the system may combine 432 the unfiltered signal 414 or the filtered signal 1231 representing the measured electrolyte concentration reflecting the concentration of ascorbic acid with the corrected percentage concentration 424 from the refractometry in order to generate a corrective bias value 1233. If the corrective bias value 1233 over time becomes larger that a threshold value that may represent the uncertainty range of measurements based on electrical conductivity, a switch 440 may close and allow for the combining 434 of the estimated sugar concentration bias 1233 with the corrected percentage concentration 424 to generate a corrected ascorbate concentration measurement 1235. Other embodiments for the exemplary portion 1200 of the system include the outputs of the three measurement subsystems, i.e., calcium ion-specific electrode, electrical conductivity measuring device, and refractometry, electronically weighted based on minimizing statistical variances and bias effects, and the weighted measurement combined to produce the corrected ascorbate measurement concentration.

Although this invention has been disclosed in the context of certain embodiments and examples, it will be understood by those of ordinary skill in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of ordinary skill in the art based upon this disclosure. It is also contemplated that various combinations or subcombinations of the specific features and aspects of the embodiments may be made and still fall within the scope of the invention. The embodiments of the present invention may be embodied in a set of program instructions, e.g., software, hardware, or both—i.e., firmware. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

What is claimed is:

1. A process for controlling ascorbate concentration of fresh produce treatment comprising:
   providing a fresh produce treatment comprised of water and ascorbate;
   measuring via a refractometer, a first ascorbate concentration, derived via a refractive index, in a first sample comprised of the fresh produce treatment;
   measuring via an electrical conductivity sensor, a second ascorbate concentration in at least one of: the first sample comprised of the fresh produce treatment and a second sample comprised of the fresh produce treatment;
   generating a measured ascorbate concentration based on the first measured ascorbate concentration and the second measured ascorbate concentration;
   comparing the measured ascorbate concentration with a control set point value to generate a difference value; and
   if the difference value is above a threshold, then feeding ascorbate into the fresh produce treatment.

2. The process of claim 1 wherein the step of feeding ascorbate into the fresh produce treatment comprises feeding ascorbate in incremental amounts via a pulsed valve.

3. The process of claim 1 wherein the step of feeding ascorbate into the fresh produce treatment comprises feeding ascorbate in incremental amounts via a pulsed valve executing pulses proportionally cycled based on the difference value.

4. The process of claim 1 wherein the step of feeding ascorbate into the fresh produce treatment comprises feeding ascorbate via a pump having pumping cycles proportionally based on the difference value.

5. A process for controlling ascorbate concentration of fresh produce treatment comprising:
   providing a fresh produce treatment comprised of water and ascorbate;
   measuring via a refractometer an ascorbate concentration of a sample comprised of the fresh produce treatment derived via a refractive index;
   comparing the measured ascorbate concentration with a control set point value to generate a difference value; and
   if the difference value is above a threshold, then feeding ascorbate into the fresh produce treatment.

6. The process of claim 5 wherein the step of feeding ascorbate into the fresh produce treatment comprises feeding ascorbate in incremental amounts via a pulsed valve.

7. The process of claim 5 wherein the step of feeding ascorbate into the fresh produce treatment comprises feeding ascorbate in incremental amounts via a pulsed valve executing pulses proportionally cycled based on the difference value.

8. The process of claim 5 wherein the step of feeding ascorbate into the fresh produce treatment comprises feeding ascorbate via a pump having pumping cycles proportionally based on the difference value.

9. A process for controlling ascorbate concentration of fresh produce treatment comprising:
   providing a fresh produce treatment comprised of water, ions and ascorbic acid;
   measuring, via an electrical conductivity sensor, the ion concentration in a sample comprised of the fresh produce treatment;
   comparing the measured ion concentration with a control set point value to generate a difference value; and
   if the difference value is above a threshold, then feeding ascorbate into the fresh produce treatment.

10. The process of claim 9 wherein the step of feeding ascorbate into the fresh produce treatment comprises feeding ascorbate in incremental amounts via a pulsed valve.

11. The process of claim 9 wherein the step of feeding ascorbate into the fresh produce treatment comprises feeding ascorbate in incremental amounts via a pulsed valve executing pulses proportionally cycled based on the difference value.

12. The process of claim 9 wherein the step of feeding ascorbate into the fresh produce treatment comprises feeding ascorbate via a pump having pumping cycles proportionally based on the difference value.

13. A process for controlling calcium ascorbate concentration of fresh produce treatment comprising:
   providing a fresh produce treatment comprised of water, calcium ions and ascorbic acid;
   measuring, via a calcium ion-specific sensor, a calcium ion concentration in a sample comprised of the fresh produce treatment;
   comparing the measured calcium ion concentration with a control set point value to generate a difference value; and
   if the difference value is above a threshold, then feeding calcium ascorbate into the fresh produce treatment.

14. The process of claim 13 wherein the step of feeding calcium ascorbate into the fresh produce treatment comprises feeding calcium ascorbate in incremental amounts via a pulsed valve.

15. The process of claim 13 wherein the step of feeding calcium ascorbate into the fresh produce treatment comprises feeding calcium ascorbate in incremental amounts via a pulsed valve executing pulses proportionally cycled based on the difference value.

16. The process of claim 13 wherein the step of feeding calcium ascorbate into the fresh produce treatment comprises feeding calcium ascorbate via a pump having pumping cycles proportionally based on the difference value.

17. A process for controlling ascorbate concentration of fresh produce treatment comprising:
   providing a fresh produce treatment comprised of water and ascorbate;
   measuring via a refractometer, a first ascorbate concentration, derived via a refractive index, in a first sample comprised of the fresh produce treatment;
   measuring via an electrical conductivity, a second ascorbate concentration in at least one of: the first sample comprised of the fresh produce treatment and a second sample comprised of the fresh produce treatment;
   measuring via a calcium ion-specific electrode, a third ascorbate concentration in a least one of: the first sample comprised of a fresh produce treatment, the second sample comprised of the fresh produce treatment, and a third sample comprised of the fresh produce treatment;
   adjusting the second ascorbate concentration measurement based on the third ascorbate concentration measurement;
   generating a measured ascorbate concentration based on the first measured ascorbate concentration and the adjusted second measured ascorbate concentration;
   comparing the measured ascorbate concentration with a control set point value to generate a difference value; and
   if the difference value is above a threshold, then feeding ascorbate into the fresh produce treatment.

18. The process of claim 17 wherein the step of feeding ascorbate into the fresh produce treatment comprises feeding ascorbate in incremental amounts via a pulsed valve.

19. The process of claim 17 wherein the step of feeding ascorbate into the fresh produce treatment comprises feeding ascorbate in incremental amounts via a pulsed valve executing pulses proportionally cycled based on the difference value.

20. The process of claim 17 wherein the step of feeding ascorbate into the fresh produce treatment comprises feeding ascorbate via a pump having pumping cycles proportionally based on the difference value.

21. A process for controlling ascorbate concentration of fresh produce treatment comprising:
   measuring via a refractometer, a first ascorbate concentration derived via a refractive index in a first sample, the first sample comprising a fresh produce treatment, wherein the fresh produce treatment comprises water and ascorbate;
   measuring via an electrical conductivity sensor, a second ascorbate concentration in at least one of: the first sample comprised of the fresh produce treatment and a second sample comprised of the fresh produce treatment;
   generating a measured ascorbate concentration based on the first measured ascorbate concentration and the second measured ascorbate concentration;
   comparing the measured ascorbate concentration with a control set point value to generate a difference value; and
   if the difference value is above a threshold, then feeding ascorbate into the fresh produce treatment.

22. The process of claim 21 wherein the step of feeding ascorbate into the fresh produce treatment comprises feeding ascorbate in incremental amounts via a pulsed valve.

23. The process of claim 21 wherein the step of feeding ascorbate into the fresh produce treatment comprises feeding ascorbate in incremental amounts via a pulsed valve executing pulses proportionally cycled based on the difference value.

24. The process of claim 21 wherein the step of feeding ascorbate into the fresh produce treatment comprises feeding ascorbate via a pump having pumping cycles proportionally based on the difference value.

25. A process for controlling ascorbate concentration of fresh produce treatment comprising:
   measuring via a refractometer an ascorbate concentration derived via a refractive index of a sample, the sample comprising a fresh produce treatment wherein the fresh produce treatment comprises water and ascorbate;
   comparing the measured ascorbate concentration with a control set point value to generate a difference value; and
   if the difference value is above a threshold, then feeding ascorbate into the fresh produce treatment.

26. The process of claim 25 wherein the step of feeding ascorbate into the fresh produce treatment comprises feeding ascorbate in incremental amounts via a pulsed valve.

27. The process of claim 24 wherein the step of feeding ascorbate into the fresh produce treatment comprises feeding ascorbate in incremental amounts via a pulsed valve executing pulses proportionally cycled based on the difference value.

28. The process of claim 25 wherein the step of feeding ascorbate into the fresh produce treatment comprises feeding ascorbate via a pump having pumping cycles proportionally based on the difference value.

29. A process for controlling ascorbate concentration of fresh produce treatment comprising:
   measuring, via an electrical conductivity sensor, an ion concentration in a sample comprised of a fresh produce treatment, wherein the fresh produce treatment comprises water, ions, and ascorbic acid;
   comparing the measured ion concentration with a control set point value to generate a difference value; and
   if the difference value is above a threshold, then feeding ascorbate into the fresh produce treatment.

30. The process of claim 29 wherein the step of feeding ascorbate into the fresh produce treatment comprises feeding ascorbate in incremental amounts via a pulsed valve.

31. The process of claim 29 wherein the step of feeding ascorbate into the fresh produce treatment comprises feeding ascorbate in incremental amounts via a pulsed valve executing pulses proportionally cycled based on the difference value.

32. The process of claim 29 wherein the step of feeding ascorbate into the fresh produce treatment comprises feeding ascorbate via a pump having pumping cycles proportionally based on the difference value.

33. A process for controlling calcium ascorbate concentration of fresh produce treatment comprising:
   measuring, via a calcium ion-specific sensor, a calcium ion concentration in a sample comprised of a fresh produce treatment wherein the fresh produce treatment comprises water, calcium ions and ascorbic acid;
   comparing the measured calcium ion concentration with a control set point value to generate a difference value; and
   if the difference value is above a threshold, then feeding calcium ascorbate into the fresh produce treatment.

34. The process of claim 33 wherein the step of feeding calcium ascorbate into the fresh produce treatment comprises feeding calcium ascorbate in incremental amounts via a pulsed valve.

35. The process of claim 33 wherein the step of feeding calcium ascorbate into the fresh produce treatment comprises feeding calcium ascorbate in incremental amounts via a pulsed valve executing pulses proportionally cycled based on the difference value.

36. The process of claim 33 wherein the step of feeding calcium ascorbate into the fresh produce treatment comprises feeding calcium ascorbate via a pump having pumping cycles proportionally based on the difference value.

37. A process for controlling ascorbate concentration of fresh produce treatment comprising:
   measuring via a refractometer a first ascorbate concentration derived via a refractive index of a first sample, the first sample comprising a fresh produce treatment, wherein the fresh produce treatment comprises water and ascorbate;
   measuring via an electrical conductivity, a second ascorbate concentration in at least one of: the first sample comprised of the fresh produce treatment and a second sample comprised of the fresh produce treatment;
   measuring via a calcium ion-specific electrode, a third ascorbate concentration in a least one of: the first sample comprised of the fresh produce treatment, the second sample comprised of the fresh produce treatment, and a third sample comprised of the fresh produce treatment;
   adjusting the second ascorbate concentration measurement based on the third ascorbate concentration measurement;
   generating a measured ascorbate concentration based on the first measured ascorbate concentration and the adjusted second measured ascorbate concentration;
   comparing the measured ascorbate concentration with a control set point value to generate a difference value; and
   if the difference value is above a threshold, then feeding ascorbate into the fresh produce treatment.

38. The process of claim 37 wherein the step of feeding ascorbate into the fresh produce treatment comprises feeding ascorbate in incremental amounts via a pulsed valve.

39. The process of claim 37 wherein the step of feeding ascorbate into the fresh produce treatment comprises feeding ascorbate in incremental amounts via a pulsed valve executing pulses proportionally cycled based on the difference value.

40. The process of claim 37 wherein the step of feeding ascorbate into the fresh produce treatment comprises feeding ascorbate via a pump having pumping cycles proportionally based on the difference value.

* * * * *